US012678042B2

(12) United States Patent
Okada et al.

(10) Patent No.: US 12,678,042 B2
(45) Date of Patent: Jul. 14, 2026

(54) OPHTHALMOLOGIC APPARATUS AND METHOD OF EXAMINING EYE TO BE EXAMINED

(71) Applicant: TOPCON CORPORATION, Tokyo (JP)

(72) Inventors: Hiroaki Okada, Tokyo (JP); Yoko Tatara, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 242 days.

(21) Appl. No.: 18/283,586

(22) PCT Filed: Feb. 17, 2022

(86) PCT No.: PCT/JP2022/006301
§ 371 (c)(1),
(2) Date: Sep. 22, 2023

(87) PCT Pub. No.: WO2022/209387
PCT Pub. Date: Oct. 6, 2022

(65) Prior Publication Data
US 2024/0156339 A1 May 16, 2024

(30) Foreign Application Priority Data

Mar. 31, 2021 (JP) ................................. 2021059896

(51) Int. Cl.
*A61B 3/10* (2006.01)
*A61B 3/103* (2006.01)
*A61B 3/107* (2006.01)

(52) U.S. Cl.
CPC ............ *A61B 3/102* (2013.01); *A61B 3/1005* (2013.01); *A61B 3/103* (2013.01); *A61B 3/107* (2013.01)

(58) Field of Classification Search
CPC ....... A61B 3/102; A61B 3/1005; A61B 3/103; A61B 3/107; A61B 3/18
(Continued)

(56) References Cited

U.S. PATENT DOCUMENTS

2012/0162606 A1\* 6/2012 Nakamura ............. A61B 3/032
351/221
2015/0272436 A1\* 10/2015 Hayashi ................. A61B 3/107
351/208
(Continued)

FOREIGN PATENT DOCUMENTS

EP 4209170 A1 \* 7/2023 .............. A61B 3/14
JP 2017099532 A 6/2017
(Continued)

OTHER PUBLICATIONS

International Search Report from corresponding International Application No. PCT/JP2022/006301, mailed on May 10, 2022, 4 pages with translation.
(Continued)

*Primary Examiner* — Mohammed A Hasan
(74) *Attorney, Agent, or Firm* — Tucker Ellis LLP

(57) ABSTRACT

An ophthalmologic apparatus includes a first left eye measurement optical system for measurement of dimensional information in a front-back direction of a left eye, a second left eye measurement optical system for measurement of a corneal shape of the left eye, a third left eye measurement optical system for measurement of a refractive property of the left eye, a first right eye measurement optical system for measurement of dimensional information in a front-back direction of a right eye, a second right eye measurement optical system for measurement of a corneal shape of the right eye, a third right eye measurement optical system for measurement of a refractive property of the right eye, and a control unit to control the first, second and third left eye
(Continued)

measurement optical systems and the first, second and third
right eye measurement optical systems.

16 Claims, 8 Drawing Sheets

(58) Field of Classification Search
USPC ......................................................... 351/206
See application file for complete search history.

(56) References Cited

U.S. PATENT DOCUMENTS

| | | | |
|---|---|---|---|
| 2018/0064339 A1 | 3/2018 | Takii | |
| 2020/0046220 A1 | 2/2020 | Tatara | |
| 2020/0100673 A1* | 4/2020 | Shimizu | A61B 3/1225 |
| 2020/0229691 A1 | 7/2020 | Steinmueller | |

FOREIGN PATENT DOCUMENTS

| | | | | | |
|---|---|---|---|---|---|
| JP | 2018038481 A | * | 3/2018 | | |
| JP | 2019062939 A | * | 4/2019 | | |
| JP | 2019213751 A | | 12/2019 | | |
| JP | 2020121114 A | * | 8/2020 | | A61B 3/1005 |

OTHER PUBLICATIONS

Extended European Search Report from corresponding Application
No. 22779614.1 mailed on Feb. 17, 2025, 13 pages.
Chinese Office Action from corresponding Application No.
202280023860.X, mailed on May 15, 2026, 35 pages with transla-
tion.

* cited by examiner

FIG.7

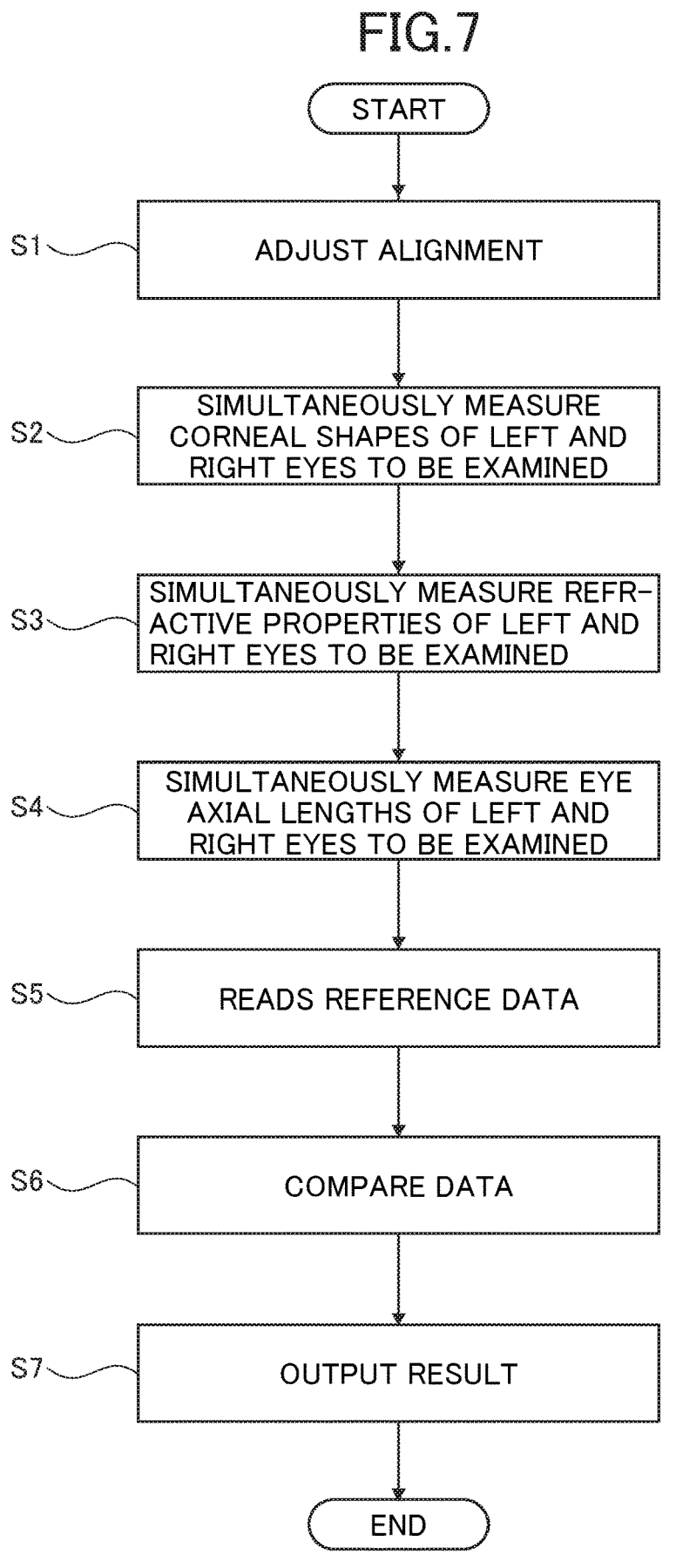

START

S1 — ADJUST ALIGNMENT

S2 — SIMULTANEOUSLY MEASURE CORNEAL SHAPES OF LEFT AND RIGHT EYES TO BE EXAMINED

S3 — SIMULTANEOUSLY MEASURE REFR-ACTIVE PROPERTIES OF LEFT AND RIGHT EYES TO BE EXAMINED

S4 — SIMULTANEOUSLY MEASURE EYE AXIAL LENGTHS OF LEFT AND RIGHT EYES TO BE EXAMINED

S5 — READS REFERENCE DATA

S6 — COMPARE DATA

S7 — OUTPUT RESULT

END

OPHTHALMOLOGIC APPARATUS AND METHOD OF EXAMINING EYE TO BE EXAMINED

CROSS-REFERENCE TO RELATED APPLICATIONS

This application claims priority based on Japanese Patent Application No. 2021-059896 filed with the Japan Patent Office on Mar. 31, 2021, the entire disclosure of which is entirely incorporated herein by reference.

TECHNICAL FIELD

The present invention relates to an ophthalmologic apparatus and a method of examining an eye to be examined.

BACKGROUND ART

Conventionally, there has been known an ophthalmologic apparatus that simultaneously performs measurement of an eye axial length of an eye to be examined, measurement of a corneal shape of the eye to be examined, and measurement of a refractive property of the eye to be examined (e.g., refer to JP 2020-121114A).

SUMMARY

By the way, a human visually recognizes an object with both left and right eyes in daily life. Therefore, in a case where eye characteristics of an eye to be examined such as an eye axial length are measured for each eye, the measurement is performed in a state in which the eye to be examined is accommodated or converged in a different state from that when both eyes look at an object. In addition, when eye characteristics of left and right eyes to be examined are measured at different timings, conditions such as a measurement environment are different. Therefore, there arises a problem in that it is difficult to appropriately measure the eye characteristics.

The present invention has been made in view of the above problems, and an object of the present invention is to provide an ophthalmologic apparatus and a method of examining an eye to be examined capable of measuring eye characteristics of left and right eyes to be examined under the same conditions in a state in which both the eyes are open.

In order to achieve the above object, an ophthalmologic apparatus of the present invention includes: a first left eye measurement optical system used for measurement of dimensional information in a front-back direction of a left eye to be examined; a second left eye measurement optical system used for measurement of a corneal shape of the left eye to be examined; a third left eye measurement optical system used for measurement of a refractive property of the left eye to be examined; a first right eye measurement optical system used for measurement of dimensional information in a front-back direction of a right eye to be examined; a second right eye measurement optical system used for measurement of a corneal shape of the right eye to be examined; a third right eye measurement optical system used for measurement of a refractive property of the right eye to be examined; and a control unit configured to control the optical systems, and process obtained measurement data. The control unit simultaneously causes the measurement using the first left eye measurement optical system and the measurement using the first right eye measurement optical system, simultaneously causes the measurement using the second left eye measurement optical system and the measurement using the second right eye measurement optical system, and simultaneously causes the measurement using the third left eye measurement optical system and the measurement using the third right eye measurement optical system.

In addition, a method of examining an eye to be examined of the present invention is a method of examining an eye to be examined by an ophthalmologic apparatus including: a first left eye measurement optical system used for measurement of dimensional information in a front-back direction of a left eye to be examined; a second left eye measurement optical system used for measurement of a corneal shape of the left eye to be examined; a third left eye measurement optical system used for measurement of a refractive property of the left eye to be examined; a first right eye measurement optical system used for measurement of dimensional information in a front-back direction of a right eye to be examined; a second right eye measurement optical system used for measurement of a corneal shape of the right eye to be examined; a third right eye measurement optical system used for measurement of a refractive property of the right eye to be examined; and a control unit configured to control the optical systems, and process obtained measurement data. The method includes: a first measurement step of simultaneously performing the measurement using the first left eye measurement optical system and the measurement using the first right eye measurement optical system; a second measurement step of simultaneously performing the measurement using the second left eye measurement optical system and the measurement using the second right eye measurement optical system; and a third measurement step of simultaneously performing the measurement using the third left eye measurement optical system and the measurement using the third right eye measurement optical system.

BRIEF DESCRIPTION OF DRAWINGS

FIG. 7 is a flowchart illustrating a procedure flow of eye characteristic measurement performed in the ophthalmologic apparatus of the first embodiment.

DESCRIPTION OF EMBODIMENTS

Figure 1:
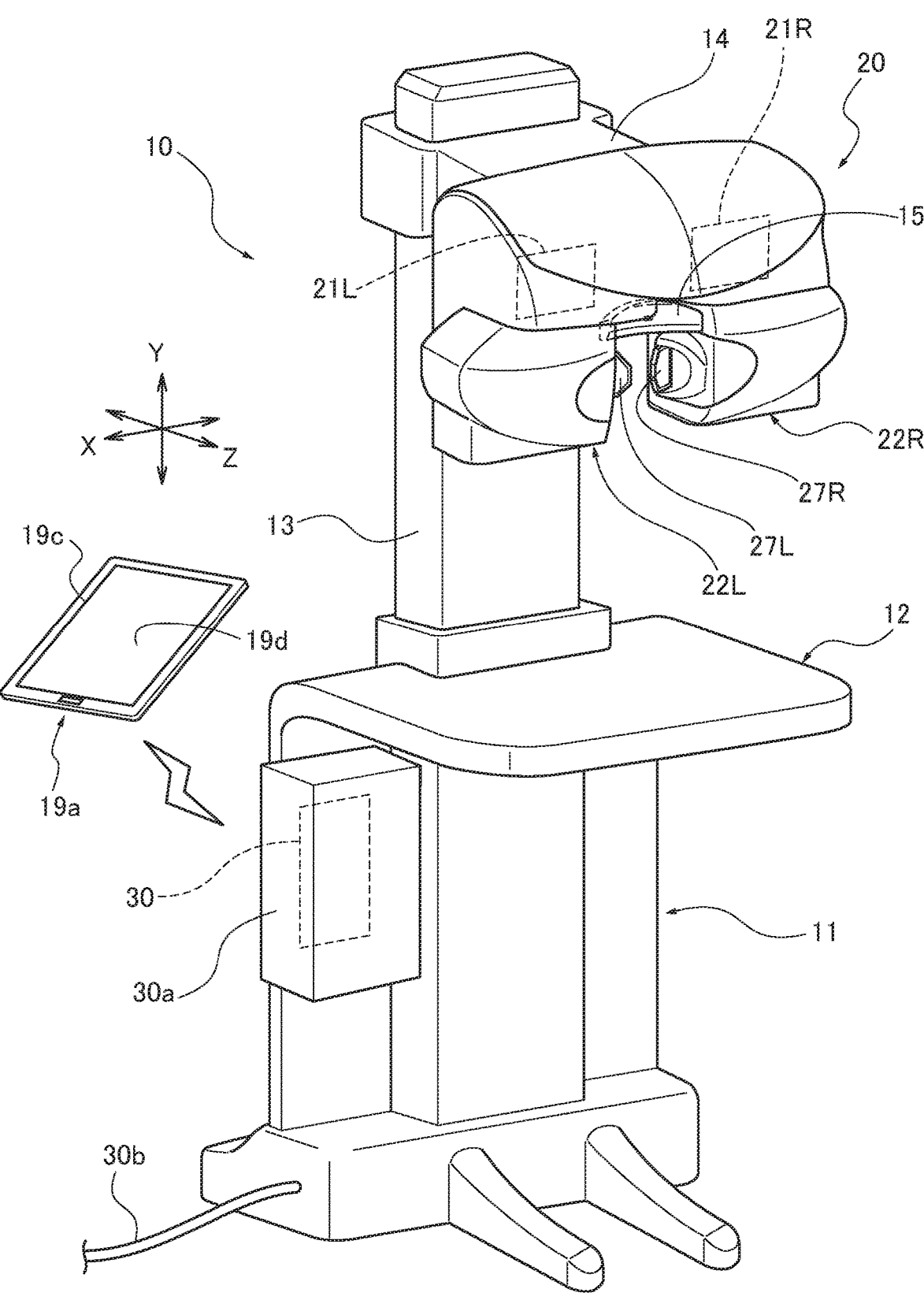
FIG. 1 is a perspective view illustrating an appearance of an ophthalmologic apparatus of a first embodiment.

With respect to the use of plural and/or singular terms herein, those having skill in the art can translate from the plural to the singular and/or from the singular to the plural as is appropriate to the context and/or application. The various singular/plural permutations may be expressly set forth herein for sake of clarity.

Hereinafter, a mode for carrying out an ophthalmologic apparatus and a method of examining an eye to be examined of the present invention will be described on the basis of a first embodiment illustrated in the drawings.

An ophthalmologic apparatus 10 of the first embodiment is a binocular open-type ophthalmologic apparatus capable of simultaneously measuring eye characteristics of both eyes to be examined in a state in which an examinee opens his/her left and right eyes.

As illustrated in FIG. 1, the ophthalmologic apparatus 10 of the first embodiment includes a base 11 placed on a floor surface, an optometry table 12, a support column 13, an arm 14, and a measurement unit 20. The ophthalmologic apparatus 10 also includes an examiner controller 19a such as a portable terminal, an examinee controller 19b (see FIG. 6), and a display device 19c such as a liquid crystal display, as input and output devices. In the first embodiment, the display device 19c is provided in the examiner controller 19a.

The ophthalmologic apparatus 10 measures eye characteristics of eyes to be examined in a state in which an examinee facing the optometry table 12 puts his/her forehead into contact with a forehead contact portion 15 that is provided in the measurement unit 20. Hereinafter, a left-right direction as viewed from the examinee is defined as an X direction, a top-bottom direction (vertical direction) is defined as a Y direction, and a direction (depth direction) orthogonal to the X direction and the Y direction is defined as a Z direction.

The optometry table 12 is supported by the base 11, and its height position can be adjusted. The support column 13 is erected in the Y direction from a rear end portion of the optometry table 12, and the arm 14 is provided on an upper portion of the support column 13. The arm 14 suspends and supports the measurement unit 20 above the optometry table 12, and extends along the Z direction from the support column 13. The arm 14 is attached to the support column 13 so as to be vertically movable.

A control box 30a that houses a control unit 30 is provided below the optometry table 12. As will be described later, the control unit 30 integrally controls operations of respective units of the ophthalmologic apparatus 10. Note that a commercial power supply (not illustrated) supplies power to the control unit 30 through a power cable 30b.

The measurement unit 20 is controlled by the control unit 30, to measure dimensional information in a front-back direction of the eyes to be examined, corneal shapes of the eyes to be examined, and refractive properties of the eyes to be examined, which are the eye characteristics of the eyes to be examined, simultaneously on the left and right sides. Note that the measurement unit 20 may perform any subjective examination or any objective measurement other than the above measurements. In the subjective examination, a visual target or the like is presented to the examinee, and an examination result is acquired on the basis of a response of the examinee to the presented visual target or the like. Examples of the subjective examination include subjective refraction measurement such as farsightedness examination, nearsightedness examination, contrast examination, and glare examination, visual field examination, astigmatism axis examination, astigmatism degree examination, and the like. In addition, in the objective measurement, the eyes to be examined are irradiated with light, and information (eye characteristics) regarding the eyes to be examined is measured on the basis of a detection result of return light. The objective measurement includes measurement for acquiring the eye characteristics of the eyes to be examined, and photography for acquiring an image of the eyes to be examined. The objective measurement further includes intraocular pressure measurement, fundus photography, tomographic image photography using optical coherence tomography (hereinafter referred to as "OCT") (OCT photography), measurement using OCT, and the like.

In addition, the measurement unit 20 is connected to the control unit 30 through a control/power cable 30c (see FIG. 2), and power is supplied thereto through the control unit 30. Transmission and reception of information between the measurement unit 20 and the control unit 30 are also performed through the control/power cable 30c.

Figure 2:
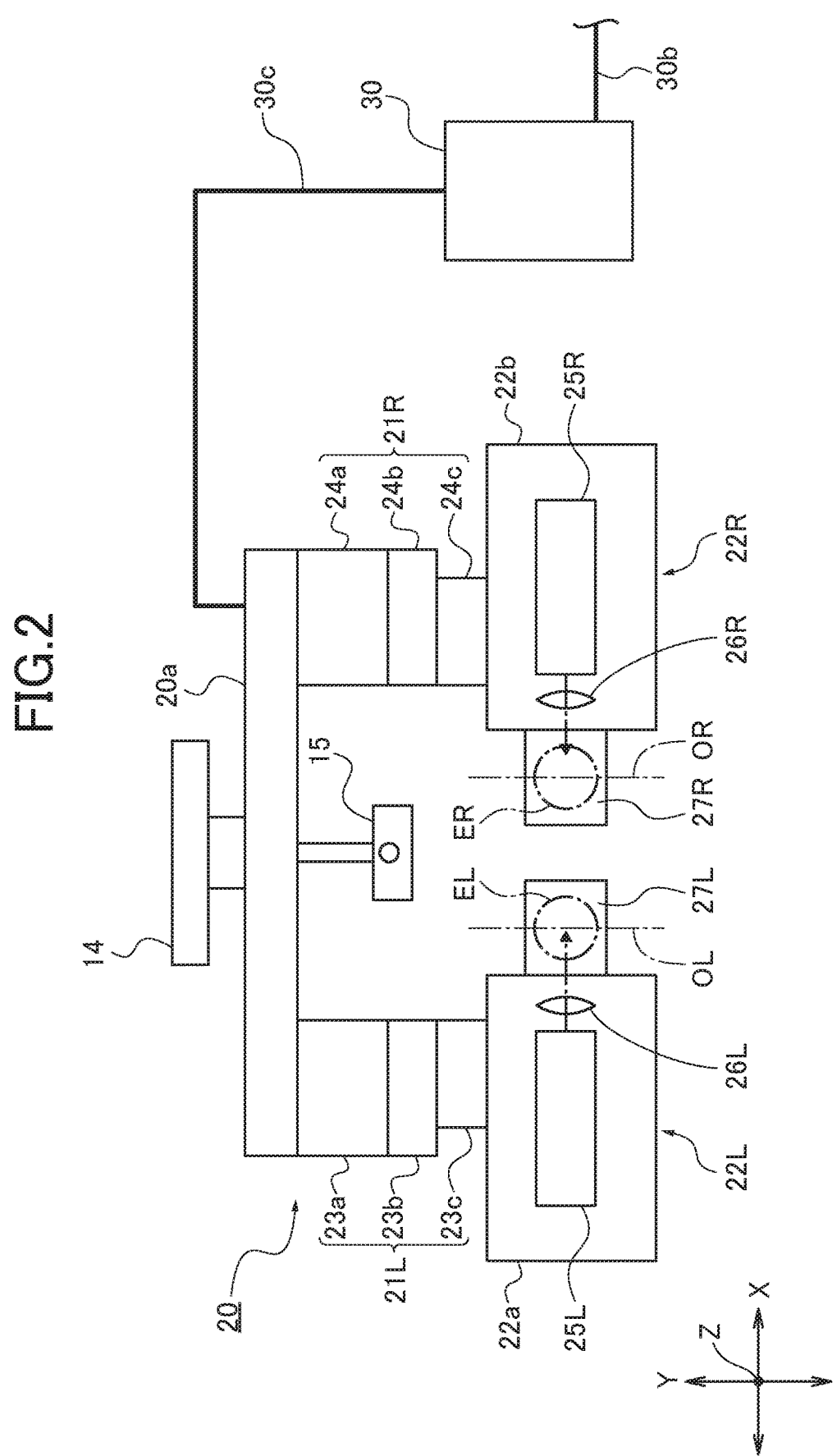
FIG. 2 is an explanatory diagram schematically illustrating a configuration of a measurement unit of the ophthalmologic apparatus of the first embodiment.

As illustrated in FIG. 2, the measurement unit 20 includes an attachment base portion 20a, a left drive mechanism 21L and a right drive mechanism 21R provided on the attachment base portion 20a, a left eye measurement head 22L supported by the left drive mechanism 21L, and a right eye measurement head 22R supported by the right drive mechanism 21R.

The left eye measurement head 22L and the right eye measurement head 22R are provided in a pair so as to individually correspond to left and right eyes to be examined EL and ER (see FIG. 2), and are configured to be plane-symmetric with respect to a vertical plane located in the middle of these heads in the X direction. In addition, each driver of the left drive mechanism 21L supporting the left eye measurement head 22L and each driver of the right drive mechanism 21R supporting the right eye measurement head 22R are configured to be plane-symmetric with respect to a vertical plane located in the middle of these drives in the X direction.

The left drive mechanism 21L includes a left vertical driver 23a, a left horizontal driver 23b, and a left revolution driver 23c, and is suspended from one end of the attachment base portion 20a. The drivers 23a, 23b, and 23c are disposed between the attachment base portion 20a and the left eye measurement head 22L in the order of the left vertical driver 23a, the left horizontal driver 23b, and the left revolution driver 23c from an upper side.

The right drive mechanism 21R includes a right vertical driver 24a, a right horizontal driver 24b, and a right revolution driver 24c, and is suspended from the other end of the attachment base portion 20a. The drivers 24a, 24b, and 24c are disposed between the attachment base portion 20a and the right eye measurement head 22R in the order of the right vertical driver 24a, the right horizontal driver 24b, and the right revolution driver 24c from an upper side.

Each of the drivers 23a, 23b, 23c, 24a, 24b, and 24c includes an actuator that generates a drive force, such as a pulse motor, and a transmission mechanism that transmits the drive force, such as a plurality of gear sets and a rack and pinion.

The left vertical driver 23a moves the left eye measurement head 22L in the Y direction (vertical direction) with respect to the attachment base portion 20a, and the right vertical driver 24a moves the right eye measurement head 22R in the Y direction (vertical direction) with respect to the attachment base portion 20a. In addition, the left horizontal driver 23b moves the left eye measurement head 22L in the X direction and the Z direction (horizontal direction) with respect to the attachment base portion 20a, and the right horizontal driver 24b moves the right eye measurement head 22R in the X direction and the Z direction (horizontal direction) with respect to the attachment base portion 20a.

The left revolution driver 23c turns the left eye measurement head 22L around an eyeball revolution axis OL (see FIG. 2) of the left eye to be examined EL, to change a direction of the left eye measurement head 22L with respect to the left eye to be examined EL. In addition, the right revolution driver 24c turns the right eye measurement head 22R around an eyeball revolution axis OR (see FIG. 2) of the right eye to be examined ER, to change a direction of the right eye measurement head 22R with respect to the right eye to be examined ER.

Note that the left horizontal driver 23b and the right horizontal driver 24b may be provided with a combination of the actuator and the transmission mechanism in each of the X direction and the Z direction. In this case, the configuration can be simplified and the movement in the horizontal direction can be easily controlled. In addition, the left revolution driver 23c and the right revolution driver 24c move the transmission mechanisms receiving the drive forces from the actuators, along arc-shaped guide grooves having the eyeball revolution axes OL and OR as center positions. As a result, the left eye measurement head 22L and the right eye measurement head 22R are turned around the eyeball revolution axis OL of the left eye to be examined EL and the eyeball revolution axis OR of the right eye to be examined ER, respectively. The left eye measurement head 22L and the right eye measurement head 22R may be attached to the left revolution driver 23c and the right revolution driver 24c so as to be turnable around turning axes of the left revolution driver 23c and the right revolution driver 24c.

Figure 3A:
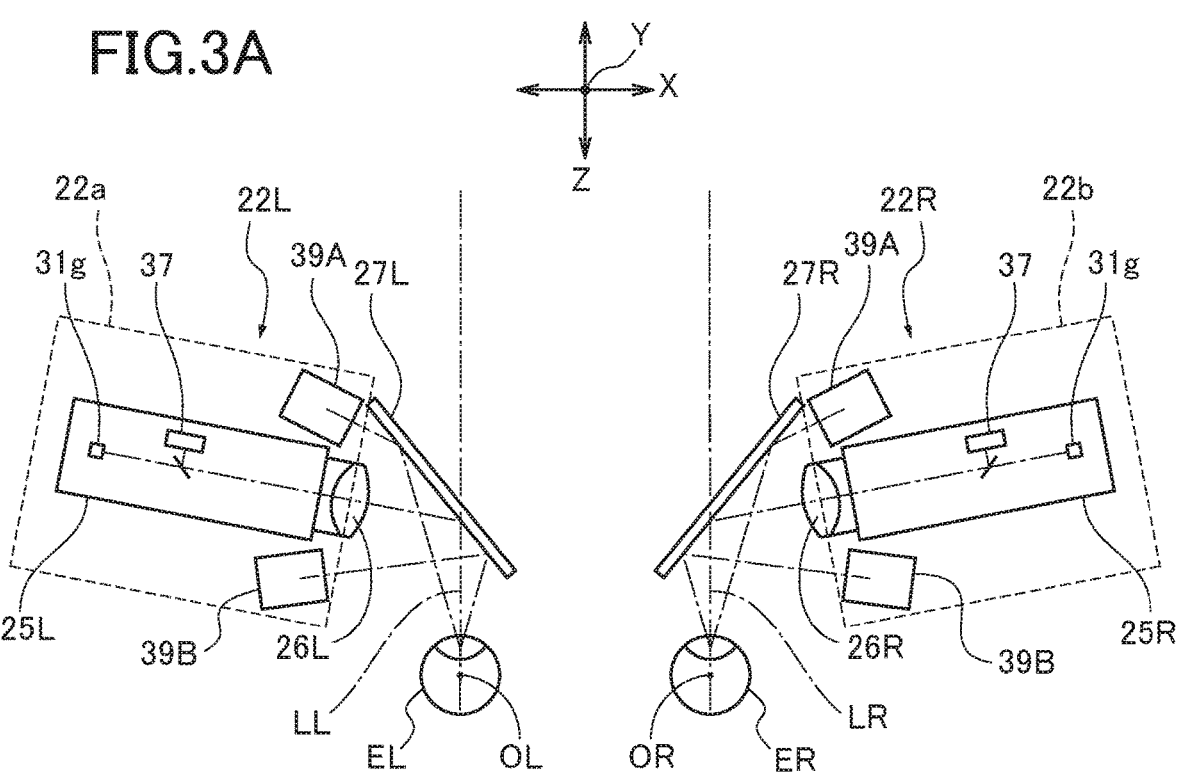
FIG. 3A is an explanatory diagram schematically illustrating a configuration of a measurement optical system of the ophthalmologic apparatus of the first embodiment, illustrating a state in which both eyes look at infinity.
Figure 3B:
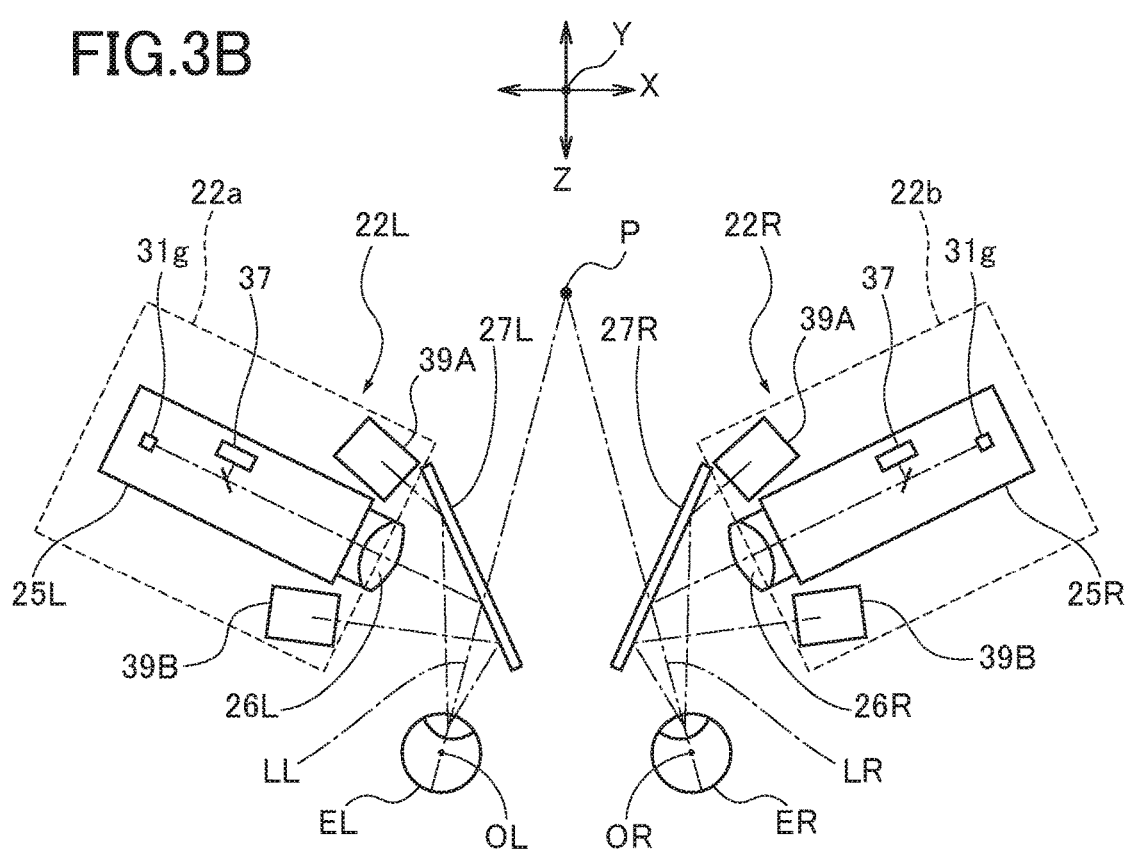
FIG. 3B is an explanatory diagram schematically illustrating a configuration of the measurement optical system of the ophthalmologic apparatus of the first embodiment, illustrating a state in which both eyes look at a predetermined position.

As illustrated in FIGS. 2, 3A, and 3B, the left eye measurement head 22L includes a left housing 22a (left-eye housing) fixed to the left revolution driver 23c, a left eye measurement optical system 25L and an objective lens 26L housed in the left housing 22a, and a left-eye deflection member 27L provided on an outer surface of the left housing 22a. Furthermore, in proximity to the left-eye deflection member 27L, two cameras (stereo cameras) 39A and 39B are provided in the left housing 22a at the front and back (Z direction) with an optical axis of the left eye measurement optical system 25L therebetween. The left eye measurement head 22L measures the eye characteristics of the left eye to be examined EL by irradiating the left eye to be examined EL with emission light emitted through the objective lens 26L from the left eye measurement optical system 25L and bent by the left-eye deflection member 27L. In addition, each of the cameras 39A and 39B acquires an anterior eye segment image (more specifically, an anterior eye segment image photographed from an oblique lateral direction intersecting a visual axis) of the left eye to be examined EL bent by the left-eye deflection member 27L and incident thereon.

As illustrated in FIGS. 2, 3A, and 3B, the right eye measurement head 22R includes a right housing 22b (right-eye housing) fixed to the right revolution driver 24c, a right eye measurement optical system 25R and an objective lens 26R housed in the right housing 22b, and a right-eye deflection member 27R provided on an outer surface of the right housing 22b. Furthermore, in proximity to the right-eye deflection member 27R, two cameras (stereo cameras) 39A and 39B are provided in the right housing 22b at the front and back (Z direction) with an optical axis of the right eye measurement optical system 25R therebetween. The right eye measurement head 22R measures the eye characteristics of the right eye to be examined ER by irradiating the right eye to be examined ER with emission light emitted through the objective lens 26R from the right eye measurement optical system 25R and bent by the right-eye deflection member 27R. In addition, each of the cameras 39A and 39B acquires an anterior eye segment image (more specifically, an anterior eye segment image photographed from an oblique lateral direction intersecting a visual axis) of the right eye to be examined ER bent by the right-eye deflection member 27R and incident thereon.

In the ophthalmologic apparatus 10 of the first embodiment, by photographing each of the eyes to be examined EL and ER substantially simultaneously from different directions by the cameras 39A and 39B, two different anterior eye segment images can be acquired for each of the eyes to be examined EL and ER. Note that the positions of the cameras 39A and 39B are not limited to the front and back with the optical axis therebetween, and may be disposed on the upper and lower sides with the optical axis therebetween. In addition, the number of cameras is not limited to two, and for example, three or more cameras may be provided, such as four cameras provided at the front and back and on the upper and lower sides. In this case, more anterior eye segment images can be acquired. Moreover, the cameras 39A and 39B may be provided outside each of the housings 22a and 22b, and can be disposed at desired positions according to the size, design, and the like of each unit.

Here, "substantially simultaneously" means that a photographing timing deviation to such an extent that eyeball movements can be ignored is allowed in the photographing by the plurality of cameras 39A and 39B. By substantially simultaneously photographing an anterior eye segment of each of the eyes to be examined EL and ER from different directions by the plurality of cameras 39A and 39B, it is possible to acquire a plurality of photographed images when each of the eyes to be examined EL and ER is at the same position (direction).

Furthermore, the ophthalmologic apparatus 10 of the first embodiment adjusts positions of the measurement heads 22L and 22R, to cause positions of the deflection members 27R and 27L to correspond to the left and right eyes to be examined EL and ER, respectively. As a result, the ophthalmologic apparatus 10 of the first embodiment can acquire upper parts (eye characteristics) of the left and right eyes to be examined EL and ER simultaneously in both the eyes in a state in which the examinee opens the left and right eyes to be examined EL and ER (in a state of binocular vision).

In addition, the respective measurement heads 22L and 22R simultaneously change their turning orientations symmetrically around the eyeball revolution axes OL and OR of the corresponding left and right eyes to be examined EL and ER. As a result, directions of a left eye measurement axis LL of the left eye measurement optical system 25L and a right eye measurement axis LR of the right eye measurement optical system 25R are changed in accordance with the visual axes (line-of-sight directions) that change due to divergence or convergence with the left and right eyes to be examined EL and ER in the state of binocular vision.

That is, FIG. 3A illustrates a state in which the turning orientations of the respective measurement heads 22L and 22R are adjusted such that the left eye measurement axis LL from the left eye to be examined EL to the left-eye deflection member 27L and the right eye measurement axis LR from the right eye to be examined ER to the right-eye deflection member 27R are parallel to each other. In the state illustrated in FIG. 3A, the visual axes can be made similar to those in a state in which the examinee looks at infinity in the state of binocular vision.

In addition, FIG. 3B illustrates a state in which the turning orientations of the respective measurement heads 22L and 22R are adjusted such that the left eye measurement axis LL from the left eye to be examined EL to the left-eye deflection member 27L and the right eye measurement axis LR from the right eye to be examined ER to the right-eye deflection member 27R are individually extended toward a predetermined position P. In the state illustrated in FIG. 3B, the visual axes can be made similar to those in a state in which the examinee looks at the predetermined position P in the state of binocular vision.

Figure 4:
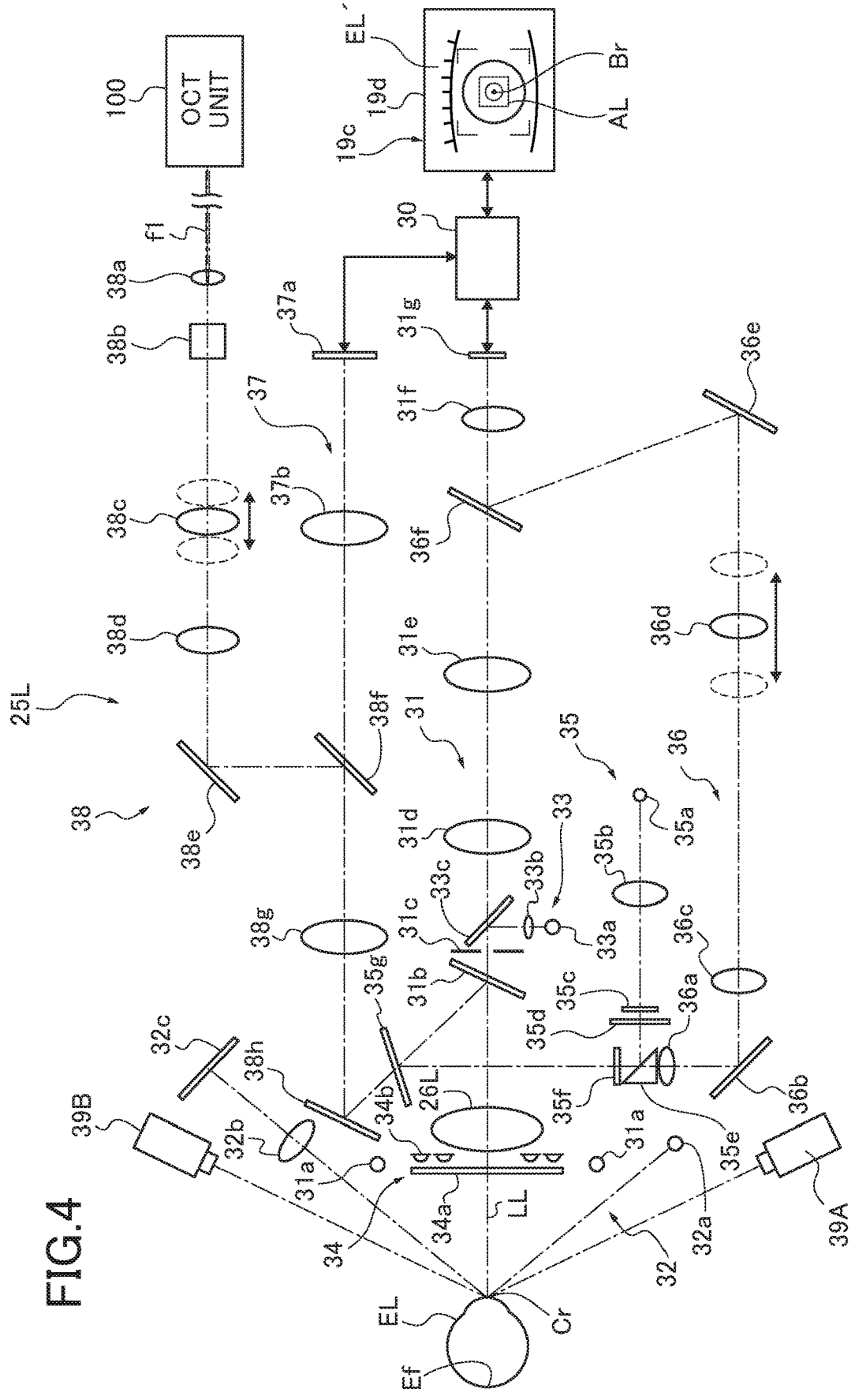
FIG. 4 is an explanatory diagram illustrating a configuration of the measurement optical system of the first embodiment.

Hereinafter, a configuration example of the left eye measurement optical system 25L and the right eye measurement optical system 25R will be described with reference to FIG. 4. Since the configuration of the left eye measurement optical system 25L and the configuration of the right eye measurement optical system 25R are identical, only the left eye measurement optical system 25L will be described below.

The left eye measurement optical system 25L of the first embodiment includes an anterior eye segment observation system 31, a Z alignment system 32, an XY alignment system 33, a keratometry system 34, a reflex measurement projection system 35, a reflex measurement light receiving system 36, a fixation projection system 37, and an OCT optical system 38. Here, the anterior eye segment observation system 31, the XY alignment system 33, the keratometry system 34, the reflex measurement projection system 35, the reflex measurement light receiving system 36, the fixation projection system 37, and the OCT optical system 38 have the common left eye measurement axis LL. In addition, the reflex measurement projection system 35 and the reflex measurement light receiving system 36 constitute a reflex measurement optical system. In the right eye measurement optical system 25R, the anterior eye segment observation system 31, the XY alignment system 33, the keratometry system 34, the reflex measurement projection system 35, the reflex measurement light receiving system 36, the fixation projection system 37, and the OCT optical system 38 have the common right eye measurement axis LR.

(Anterior Eye Segment Observation System 31)

The anterior eye segment observation system 31 is an optical system that photographs a moving image of the anterior eye segment of the left eye to be examined EL. The anterior eye segment observation system 31 includes an anterior eye segment illumination light source 31a for photographing the anterior eye segment. The anterior eye segment illumination light source 31a emits illumination light (e.g., infrared light) to the anterior eye segment of the left eye to be examined EL. Light reflected by the anterior eye segment of the left eye to be examined EL passes through the objective lens 26L, is transmitted through a dichroic mirror 31b, passes through a hole formed in a diaphragm (telecentric diaphragm) 31c, is transmitted through a half mirror 33c, sequentially passes through a relay lens 31d and a relay lens 31e, and is transmitted through a dichroic mirror 36f. The light transmitted through the dichroic mirror 36f forms an image on an imaging surface of an imaging element 31g by an image-forming lens 31f. The imaging element 31g (imaging surface) is defined as a pupil conjugate position for the above-described optical system through the anterior eye segment observation system 31. The imaging element 31g captures an image at a predetermined rate and outputs a video signal to the control unit 30. The control unit 30 displays a left anterior eye segment image EL' based on the video signal, on a display screen 19d of the display device 19c. The left anterior eye segment image EL' is, for example, an infrared moving image.

(Z Alignment System 32)

The Z alignment system 32 is an optical system used for alignment of the left eye measurement head 22L in an optical axis direction (front-back direction, Z direction) of the anterior eye segment observation system 31. The Z alignment system 32 projects light (infrared light) emitted from a Z alignment light source 32a onto a cornea Cr of the left eye to be examined EL. The light from the Z alignment light source 32a is reflected by the cornea Cr of the left eye to be examined EL, and forms an image on a light receiving surface of a line sensor 32c by an image-forming lens 32b. In the Z alignment system 32, when a corneal apex position changes in the optical axis direction of the anterior eye segment observation system 31, a projection position of the light on the light receiving surface of the line sensor 32c is changed according to the change. The control unit 30 obtains the corneal apex position of the left eye to be examined EL on the basis of the projection position of the light on the sensor surface of the line sensor 32c, and controls the left horizontal driver 23b on the basis of the obtained position to execute Z alignment.

(XY Alignment System 33)

The XY alignment system 33 is an optical system used for alignment of the left eye measurement head 22L in a direction orthogonal to the optical axis (left-right direction (X direction), top-bottom direction (Y direction)) of the anterior eye segment observation system 31. The XY alignment system 33 projects light (infrared light) emitted from an XY alignment light source 33a onto the cornea Cr of the left eye to be examined EL. The light from the XY alignment light source 33a passes through a collimator lens 33b, and is reflected by the half mirror 33c to be projected through the anterior eye segment observation system 31. That is, the XY alignment system 33 is branched from an optical path of the anterior eye segment observation system 31 by the half mirror 33c, and shares the objective lens 26L, the dichroic mirror 31b, and the diaphragm 31c with the anterior eye segment observation system 31. Reflected light from the cornea Cr of the eye to be examined E is guided to the imaging element 31g through the anterior eye segment observation system 31.

The XY alignment system 33 forms a bright spot image Br that is an image based on the reflected light. The bright spot image Br is acquired by the imaging element 31g together with the left anterior eye segment image EL'. The control unit 30 displays an alignment mark AL and the left anterior eye segment image EL' including the bright spot image Br on the display screen 19d of the display device 19c. Furthermore, the control unit 30 automatically executes XY alignment by controlling the left vertical driver 23a and the left horizontal driver 23b so as to eliminate displacement of the bright spot image Br with respect to the alignment mark AL. Note that an examiner can manually perform XY alignment by performing a moving operation of the left eye measurement head 22L so as to guide the bright spot image Br into the alignment mark AL.

(Keratometry System 34)

The keratometry system 34 is an optical system used for measuring a shape of the cornea Cr of the left eye to be examined EL, and constitutes a keratometer mechanism. Note that the "corneal shape" includes at least one of a corneal curvature radius, a corneal refractive power, a corneal astigmatism degree, and a corneal astigmatism axis angle. Here, the keratometry system 34 of the left eye measurement optical system 25L corresponds to a second left eye measurement optical system, and the keratometry system 34 of the right eye measurement optical system 25R corresponds to a second right eye measurement optical system.

The keratometry system 34 includes a kerato plate 34a and a kerato ring light source 34b. The kerato plate 34a is disposed between the objective lens 26L and the left eye to be examined EL, and the kerato ring light source 34b is provided between the kerato plate 34a and the objective lens 26L. The keratometry system 34 illuminates the kerato plate 34a with light from the kerato ring light source 34b, to project a ring-shaped light flux (light flux for corneal shape measurement) onto the cornea Cr of the left eye to be examined EL. That is, the kerato plate 34a and the kerato ring light source 34b form a kerato projection system that projects a ring-shaped light flux onto the cornea Cr of the left eye to be examined EL.

Reflected light (kerato ring image: pattern image) from the cornea Cr of the left eye to be examined EL is detected by the anterior eye segment observation system 31 and acquired by the imaging element 31g together with the left anterior eye segment image EL'. The control unit 30 calculates a corneal shape parameter representing the shape of the cornea Cr by performing known computation on the basis of the kerato ring image. Furthermore, the control unit 30 obtains the corneal shape of the left eye to be examined EL on the basis of the image obtained by the anterior eye segment observation system 31.

(Reflex Measurement Optical System)

The reflex measurement optical system including the reflex measurement projection system 35 and the reflex measurement light receiving system 36 is an optical system used for measuring a refractive property of the left eye to be examined EL, and constitutes an auto refractometer mechanism. Note that the "refractive property" includes at least one of a refractive power value, a spherical degree, an astigmatism degree, and an astigmatism axis angle. Here, the reflex measurement optical system (the reflex measurement projection system 35 and the reflex measurement light receiving system 36) of the left eye measurement optical system 25L corresponds to a third left eye measurement optical system, and the reflex measurement optical system (the reflex measurement projection system 35 and the reflex measurement light receiving system 36) of the right eye measurement optical system 25R corresponds to a third right eye measurement optical system.

The reflex measurement projection system 35 includes a reflex measurement light source 35a that is a super luminescent diode (SLD) light source as a high luminance light source, and projects a measurement light flux (light flux for refractive property measurement) onto an eye fundus Ef of the left eye to be examined EL. The reflex measurement light source 35a is movable in an optical axis direction, and is disposed at a fundus conjugate position. Light output from the reflex measurement light source 35a passes through a relay lens 35b, enters a conical surface of a conical prism 35c, and is deflected to be emitted from a bottom surface of the conical prism 35c. The light from the bottom surface of the conical prism 35c passes through a light transmission portion formed in a ring shape of a ring diaphragm 35d to form a ring-shaped light flux, is reflected by a reflection surface around a hole of a holed prism 35e, passes through a rotary prism 35f, and is reflected by a filter 35g. The filter 35g is an optical element that separates an optical path of the OCT optical system 38 from an optical path of the reflex measurement optical system by performing wavelength separation. The rotary prism 35f is used for averaging a light quantity distribution of the ring-shaped light flux with respect to a blood vessel and a disease site of the eye fundus Ef, reducing speckle noise caused by the light source, and the like. The reflex measurement projection system 35 shares the dichroic mirror 31b and the objective lens 26L with the anterior eye segment observation system 31, and reflects, by the dichroic mirror 31b, the light reflected by the filter 35g to cause the light to pass through the objective lens 26L and be projected onto the left eye to be examined EL.

The reflex measurement projection system 35 is provided in an optical path branched by the holed prism 35e provided in an optical path of the reflex measurement light receiving system 36. The hole formed in the holed prism 35e is disposed at a pupil conjugate position.

The reflex measurement light receiving system 36 receives the measurement light flux (light flux for refractive property measurement, here, ring-shaped light flux) reflected from the eye fundus Ef of the left eye to be examined EL. The reflex measurement light receiving system 36 shares the dichroic mirror 31b and the objective lens 26L with the anterior eye segment observation system 31, and the reflected light (hereinafter, referred to as "fundus return light") from the eye fundus Ef passes through the objective lens 26L to be reflected by the dichroic mirror 31b and the filter 35g. In addition, the reflex measurement light receiving system 36 shares the rotary prism 35f and the holed prism 35e with the reflex measurement projection system 35, and the fundus return light passes through the rotary prism 35f and passes through the hole of the holed prism 35e. The fundus return light further passes through a relay lens 36a, is reflected by a reflection mirror 36b, and passes through a relay lens 36c and a focusing lens 36d. The focusing lens 36d is movable along an optical axis of the reflex measurement light receiving system 36. The light that has passed through the focusing lens 36d is reflected by a reflection mirror 36e, reflected by the dichroic mirror 36f, and forms an image on the imaging surface of the imaging element 31g by the image-forming lens 31f. That is, the reflex measurement light receiving system 36 shares the image-forming lens 31f and the imaging element 31g with the anterior eye segment observation system 31. In the optical system through the reflex measurement light receiving system 36, the imaging surface of the imaging element 31g is disposed at a fundus conjugate position. The control unit 30 calculates the refractive property of the left eye to be examined EL by performing known computation on the basis of the output from the imaging element 31g.

(Fixation Projection System 37)

The fixation projection system 37 is an optical system used for fixation of the left eye to be examined EL by presenting a fixation target to the left eye to be examined EL. Here, the fixation projection system 37 of the left eye measurement optical system 25L corresponds to a left eye fixation optical system, and the fixation projection system 37 of the right eye measurement optical system 25R corresponds to a right eye fixation optical system.

The fixation projection system 37 includes a liquid crystal panel 37a and a relay lens 37b, and is coupled to the optical path of the OCT optical system 38 by a dichroic mirror 38f. The fixation projection system 37 displays a pattern representing the fixation target on the liquid crystal panel 37a under the control of the control unit 30, transmits the light through the relay lens 37*b* and the dichroic mirror 38*f*, and causes the light to travel to the optical path of the OCT optical system 38. At least one of the liquid crystal panel 37*a* and the relay lens 37*b* is movable in an optical axis direction. The light transmitted through the dichroic mirror 38*f* passes through a relay lens 38*g*, is reflected by a reflection mirror 38*h*, is transmitted through the filter 35*g*, is reflected by the dichroic mirror 31*b*, and passes through the objective lens 26L to be projected onto the eye fundus Ef of the left eye to be examined EL.

The fixation projection system 37 can change a fixation position of the left eye to be examined EL by changing a display position of the pattern on the screen of the liquid crystal panel 37*a*, and can acquire various images. Examples of the image include an image centered on a yellow spot of the eye fundus Ef, an image centered on an optic disc, and an image centered on a fundus center between the yellow spot and the optic disc.

(OCT Optical System 38)

The OCT optical system 38 is an optical system used for measuring an eye axial length (dimensional information in the front-back direction) of the left eye to be examined EL by performing optical coherence tomography (OCT) measurement, and constitutes an interferometry measurement mechanism. In particular, the OCT optical system 38 of the first embodiment is an interferometer using optical coherence interferometry. In addition, here, the OCT optical system 38 of the left eye measurement optical system 25L corresponds to a first left eye measurement optical system, and the OCT optical system 38 of the right eye measurement optical system 25R corresponds to a first right eye measurement optical system. In addition, in the ophthalmologic apparatus 10 of the first embodiment, the eye axial length, which is a distance from the cornea to a retina, is measured using the OCT optical system 38. Note that the dimensional information in the front-back direction of the eye to be examined measured using the OCT optical system 38 is not limited thereto, and may be any of an anterior chamber depth that is a distance from the cornea to a crystalline lens, a crystalline lens thickness that is a thickness of the crystalline lens, and a corneal thickness that is a thickness of the cornea.

In the OCT optical system 38, a position of a focusing lens 38*c* is adjusted such that an end surface of an optical fiber f1 is conjugated with a photographed part (the eye fundus Ef or the anterior eye segment) and the optical system on the basis of a reflex measurement result performed before the OCT measurement.

The OCT optical system 38 is provided in the optical path wavelength-separated from the optical path of the reflex measurement optical system by the filter 35*g*. An optical path of the fixation projection system 37 is coupled to the optical path of the OCT optical system 38 by the dichroic mirror 38*f*. As a result, optical axes of the OCT optical system 38 and the fixation projection system 37 can be coaxially coupled together.

Figure 5:
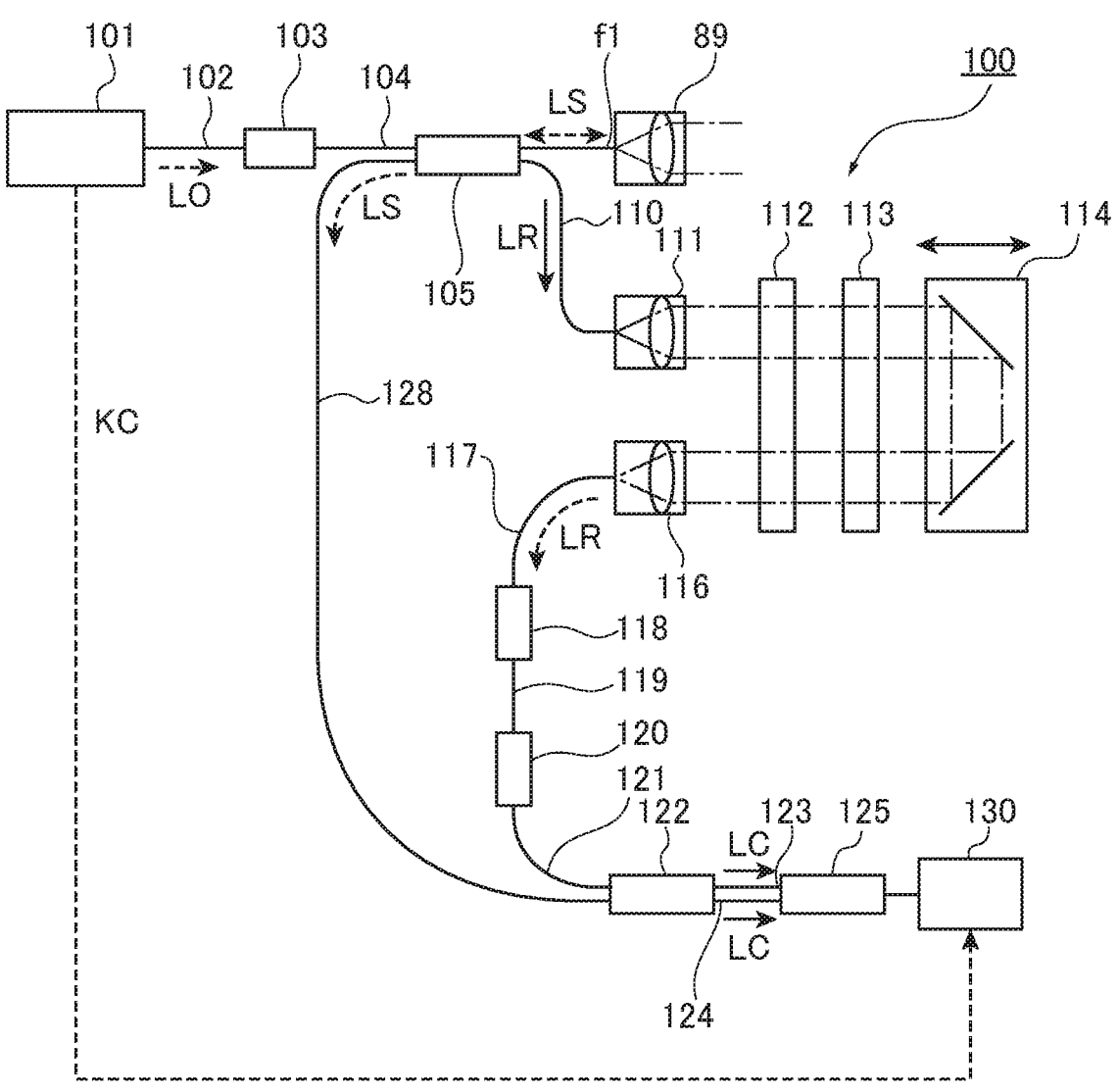
FIG. 5 is an explanatory diagram illustrating a configuration of an OCT unit of the first embodiment.

The OCT optical system 38 includes an OCT unit 100. As illustrated in FIG. 5, in the OCT unit 100, an OCT light source 101 includes a wavelength-variable light source capable of sweeping a wavelength of emission light, similarly to a general swept-source-type OCT device. The wavelength-variable light source includes a laser light source including a resonator. The OCT light source 101 temporally changes an output wavelength in a near-infrared wavelength band that cannot be visually recognized by a human eye.

As illustrated in FIG. 5, the OCT unit 100 is provided with an optical system for executing swept-source OCT. This optical system includes an interference optical system. The interference optical system has a function of splitting light from the wavelength-variable light source into measurement light and reference light, a function of generating interference light by superimposing return light of the measurement light from the eye to be examined E and the reference light passing through a reference optical path, and a function of detecting the interference light. A detection result (detection signal) of the interference light obtained by the interference optical system is a signal indicating a spectrum of the interference light, and is sent to the control unit 30. In addition, at least one of a length of an optical path (measurement arm, sample arm) of the measurement light and a length of the optical path (reference arm) of the reference light is variable.

The OCT light source 101 includes, for example, a near-infrared wavelength-variable laser that changes a wavelength (wavelength range of 1000 nm to 1100 nm) of emission light at a high speed. Light L0 output from the OCT light source 101 is guided by an optical fiber 102 to a polarization controller 103, in which its polarization state is adjusted. The light L0 whose polarization state has been adjusted is guided to a fiber coupler 105 by an optical fiber 104 and split into measurement light LS and reference light LR.

The reference light LR is guided to a collimator 111 by an optical fiber 110, converted into a parallel light flux, and guided to a corner cube 114 through an optical path length correction member 112 and a dispersion compensation member 113. The optical path length correction member 112 operates to match the optical path length of the reference light LR with the optical path length of the measurement light LS. The dispersion compensation member 113 operates to match dispersion properties of the reference light LR and of the measurement light LS. The corner cube 114 is movable in an incident direction of the reference light LR, thereby changing the optical path length of the reference light LR.

The reference light LR having passed through the corner cube 114 passes through the dispersion compensation member 113 and the optical path length correction member 112, is converted from the parallel light flux into a focused light flux by a collimator 116, and is incident on an optical fiber 117. The reference light LR incident on the optical fiber 117 is guided to a polarization controller 118 to have its polarization state adjusted, is guided to an attenuator 120 by an optical fiber 119 to have its light quantity adjusted, and is guided to a fiber coupler 122 by an optical fiber 121.

On the other hand, the measurement light LS generated by the fiber coupler 105 is guided by the optical fiber f1, converted into a parallel light flux by a collimator lens unit 38*a*, passes through an optical scanner 38*b*, the focusing lens 38*c*, a relay lens 38*d*, and a reflection mirror 38*e*, and is reflected by the dichroic mirror 38*f*.

The optical scanner 38*b* deflects the measurement light LS one-dimensionally or two-dimensionally. The optical scanner 38*b* includes, for example, a first galvano mirror and a second galvano mirror. The first galvano mirror deflects the measurement light LS so as to scan the photographed part (the eye fundus Ef or the anterior eye segment) in the horizontal direction (X direction) orthogonal to the optical axis of the OCT optical system 38. The second galvano mirror deflects the measurement light LS deflected by the first galvano mirror so as to scan the photographed part in the top-bottom direction (Y direction) orthogonal to the optical axis of the OCT optical system 38. Examples of such a scan pattern of the measurement light LS by the optical scanner 38b include horizontal scanning, vertical scanning, cross scanning, radiation scanning, circle scanning, concentric circle scanning, and spiral scanning.

The measurement light LS reflected by the dichroic mirror 38f passes through the relay lens 38g, is reflected by the reflection mirror 38h, transmitted through the filter 35g, reflected by the dichroic mirror 31b, and refracted by the objective lens 26L to be incident on the left eye to be examined EL. The measurement light LS is scattered/reflected at various depth positions of the left eye to be examined EL. Return light of the measurement light LS from the left eye to be examined EL travels in an opposite direction along the same path as the outward path, is guided to the fiber coupler 105, and reaches the fiber coupler 122 through an optical fiber 128.

The fiber coupler 122 combines (causes interference between) the measurement light LS incident through the optical fiber 128 and the reference light LR incident through the optical fiber 121 to generate interference light. The fiber coupler 122 generates a pair of beams of interference light LC by splitting the interference light at a predetermined splitting ratio (for example, 1:1). The pair of beams of interference light LC are individually guided to a detector 125 through optical fibers 123 and 124.

The detector 125 is, for example, a balanced photodiode. The balanced photodiode includes a pair of photodetectors that individually detect the pair of beams of interference light LC, and outputs a difference between a pair of detection results obtained by the photodetectors. The detector 125 sends this output (detection signal) to a data acquisition system (DAQ) 130.

The OCT light source 101 supplies a clock KC to the DAQ 130. The clock KC is generated in synchronization with an output timing of each wavelength swept within a predetermined wavelength range by the wavelength-variable light source in the OCT light source 101. For example, the OCT light source 101 optically delays one of two split light beams obtained by splitting the light L0 of each output wavelength, and then generates the clock KC on the basis of a result of detecting combined light of these light beams. The DAQ 130 samples the detection signal input from the detector 125 on the basis of the clock KC. The DAQ 130 sends a sampling result of the detection signal from the detector 125 to the control unit 30. For example, the control unit 30 forms a reflection intensity profile in each A line by performing a Fourier transform or the like on a spectrum distribution on the basis of sampling data for each series of wavelength sweeps (for each A line). Furthermore, the control unit 30 may form image data by imaging the reflection intensity profile of each A line.

Although the ophthalmologic apparatus 10 of the first embodiment is provided with the element (movable corner cube 114) that changes the reference arm length to change a difference between the measurement arm length and the reference arm length and move a coherence gate, another element may be adopted. For example, a movable mirror can be provided in the reference arm, or a movable retroreflector such as a corner cube can be provided in the measurement arm.

In addition, the control unit 30 calculates the refractive power value from the measurement result obtained using the reflex measurement optical system, and moves each of the reflex measurement light source 35a and the focusing lens 36d in the optical axis direction to the position where the eye fundus Ef, the reflex measurement light source 35a, and the imaging element 31g are conjugated on the basis of the calculated refractive power value. The control unit 30 may move the focusing lens 38c of the OCT optical system 38 in the optical axis direction in conjunction with the movement of the focusing lens 36d. That is, the OCT optical system 38 can be finely adjusted on the basis of the measurement data of the refractive property using the reflex measurement optical system.

Figure 6:
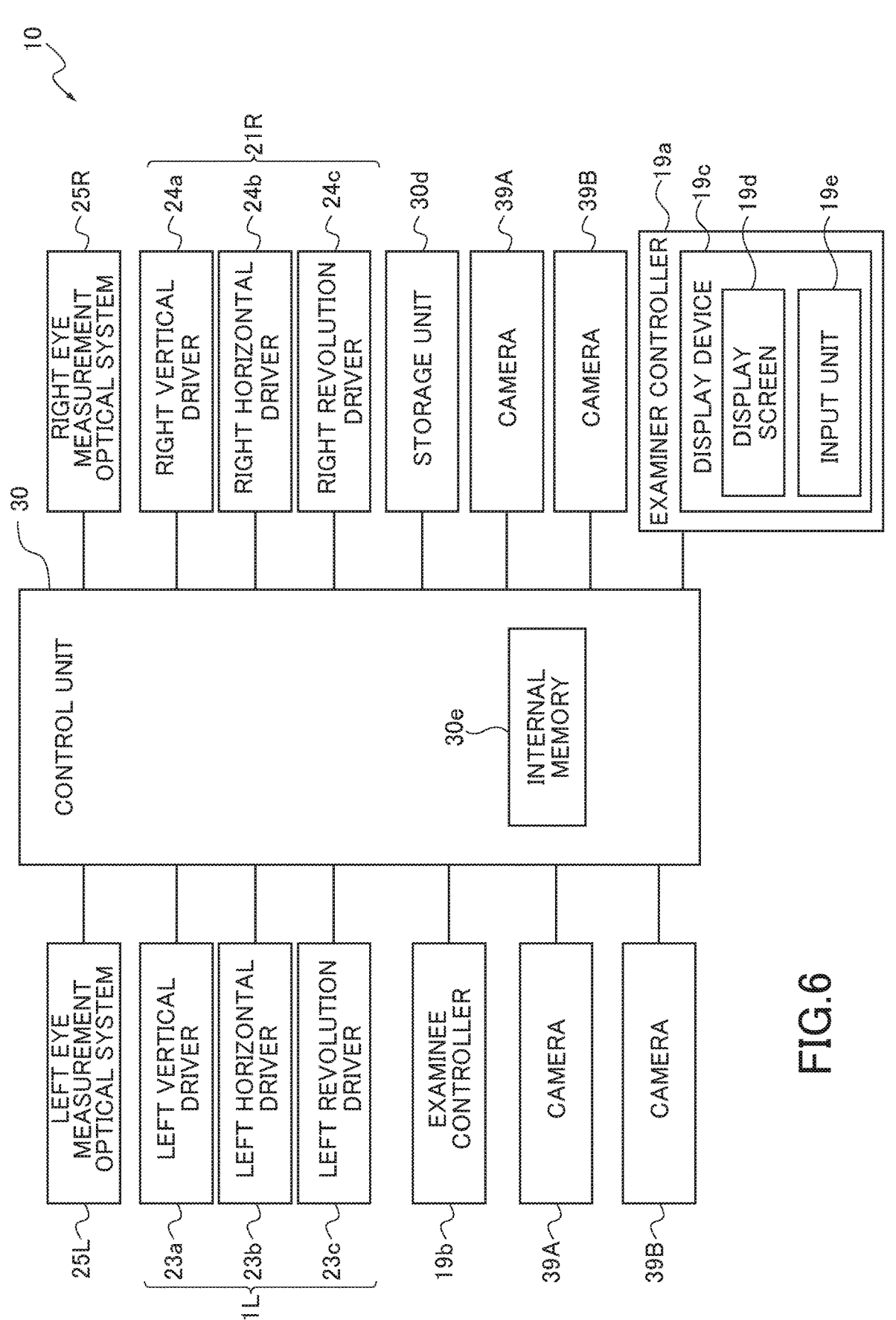
FIG. 6 is a block diagram illustrating a configuration of a control system of the ophthalmologic apparatus of the first embodiment.

As illustrated in FIG. 6, the left eye measurement optical system 25L and the right eye measurement optical system 25R, the left and right vertical drivers 23a and 24a, the left and right horizontal drivers 23b and 24b, and the left and right revolution drivers 23c and 24c as the left and right drive mechanisms 21L and 21R, the cameras 39A and 39B, the examiner controller 19a, the examinee controller 19b, and a storage unit 30d are connected to the control unit 30.

Here, the examiner controller 19a is an operation mechanism used by the examiner to operate the ophthalmologic apparatus 10. The examiner controller 19a is connected to the control unit 30 so as to be able to communicate therewith by short-range wireless communication. Although the examiner controller 19a of the first embodiment uses a portable terminal such as a tablet terminal and a smartphone, the examiner controller 19a is not limited to the configuration of the first embodiment as long as it is connected to the control unit 30 via a wired or wireless communication path. That is, the examiner controller 19a may be a notebook personal computer, a desktop personal computer, or the like, or may be fixed to the ophthalmologic apparatus 10.

In addition, the examiner controller 19a is provided with the display device 19c. The display device 19c includes the display screen 19d (see FIG. 1 and the like) on which an image and the like are displayed, and a touch panel-type input unit 19e disposed to be superimposed thereon. The examiner controller 19a appropriately displays the anterior eye segment image and the like from the anterior eye segment observation system 31, on the display screen 19d under the control of the control unit 30. In addition, the examiner controller 19a outputs operation information such as an alignment instruction and a measurement instruction input via the input unit 19e, to the control unit 30.

The examinee controller 19b is used to input an examinee's response in the acquisition of various eye characteristics of the left and right eyes to be examined EL and ER. Although not illustrated, the examinee controller 19b may be, for example, an input device such as a control lever, a keyboard, a mouse, and a portable terminal. The examinee controller 19b is connected to the control unit 30 via a wired or wireless communication path.

The control unit 30 deploys a program stored in the storage unit 30d connected thereto or in an internal memory 30e, for example, on a random access memory (RAM), thereby integrally controlling operations of the ophthalmologic apparatus 10 according to an operation of the examiner controller 19a or the examinee controller 19b as appropriate. In the first embodiment, the storage unit 30d includes a read only memory (ROM), an electrically erasable programmable ROM (EEPROM), or the like, and the internal memory 30e includes a RAM or the like.

In addition, the storage unit 30d stores various data including reference data of various eye characteristics such as the eye axial lengths, refractive properties, and corneal shapes of the eyes to be examined. Here, the "reference data" is data used for determination by comparison with measurement data, for example, statistical data (e.g., an average value or the like) obtained by performing statistical processing on measurement data of a large number of eyes to be examined, a data group corresponding to 50% of humans in a predetermined comparison group, or the like. In addition, the storage unit 30d may store various types of measurement data.

The control unit 30 aligns the left and right measurement heads 22L and 22R with the left and right eyes to be examined EL and ER, respectively, by using the Z alignment systems 32 and the XY alignment systems 33. In addition, the control unit 30 simultaneously measures the eye axial lengths of the left and right eyes to be examined EL and ER by using the OCT optical systems 38 and the two cameras 39A and 39B. In addition, the control unit 30 simultaneously measures the corneal shapes of the left and right eyes to be examined EL and ER by using the keratometry systems 34. Moreover, the control unit 30 simultaneously measures the refractive properties of the left and right eyes to be examined EL and ER by using the reflex measurement optical systems (the reflex measurement projection systems 35 and the reflex measurement light receiving systems 36).

Furthermore, the control unit 30 compares the measurement data obtained by performing each measurement described above with the reference data read from the storage unit 30d, and outputs a comparison result. Note that the comparison result is output, for example, by being displayed on the display screen 19d of the display device 19c of the examiner controller 19a.

In addition, when comparing the measurement data with the reference data, the control unit 30 may compare the measurement data in consideration of an age of the examinee, a prevalence rate of myopia in the reference data, an occupation profile and nature, and the like. This enables more accurate comparison.

In addition, the control unit 30 may store the measurement data of the examinee determined at a time point before measurement, in the storage unit 30d as the reference data. As a result, for example, the measurement data of the same examinee at different time points can be compared, a potential change in the eye characteristics of the eyes to be examined can be obtained over a predetermined period, and, for example, a cause of deterioration of the refractive properties can be easily identified.

In addition, the control unit 30 may correct the measurement data of the refractive properties of the left and right eyes to be examined EL and ER by the measurement data of the eye axial lengths of the left and right eyes to be examined EL and ER and/or the measurement data of the corneal shapes of the left and right eyes to be examined EL and ER. That is, the control unit 30 checks the validity of the measurement data of the refractive properties of the left and right eyes to be examined EL and ER on the basis of the eye axial lengths and/or corneal curvatures of the left and right eyes to be examined EL and ER. When determining that the measurement data of the refractive properties is invalid, the control unit 30 notifies the examiner that the measurement data is invalid. Note that the examiner is notified by display on the display device 19c, voice output, or the like.

Here, the refractive properties of the eyes to be examined are affected by many factors and environmental conditions, it is difficult to obtain objective refractive properties, and the refractive properties may be affected by errors. However, the measurement data of the eye axial lengths and the corneal shapes is measurement data that is not affected by, for example, a drug or a brain activity. Therefore, the validity of the measurement data of the refractive properties can be determined by the measurement data of the eye axial lengths and the corneal shapes.

Furthermore, in the ophthalmologic apparatus 10 of the first embodiment, when the eye characteristics (eye axial lengths, corneal shapes, refractive properties) of the left and right eyes to be examined EL and ER are measured, the measurement may be performed by administering a cycloplegic agent to the left and right eyes to be examined EL and ER. However, by performing the measurement without administering a cycloplegic agent, the measurement of the left and right eyes to be examined EL and ER can be performed more easily and quickly.

Hereinafter, an operation example of the ophthalmologic apparatus 10 of the first embodiment will be described on the basis of a flowchart illustrated in FIG. 7.

In step S1, after the face of the examinee is fixed by the forehead contact portion 15, the control unit 30 receives an examiner's operation on the examiner controller 19a, and turns on the Z alignment light source 32a and the XY alignment light source 33a. The control unit 30 acquires an imaging signal of the anterior eye segment image formed on the imaging surface of the imaging element 31g, and displays an anterior eye segment image E' on the display screen 19d of the display device 19c. Thereafter, the left eye measurement head 22L and the right eye measurement head 22R are moved to examination positions of the left and right eyes to be examined EL and ER. The examination positions are positions where the eye characteristics of the left and right eyes to be examined EL and ER can be measured. The left eye measurement head 22L and the right eye measurement head 22R are disposed at the examination positions through alignment by the Z alignment systems 32, the XY alignment systems 33, and the anterior eye segment observation systems 31. The control unit 30 performs the movement of the left eye measurement head 22L and the right eye measurement head 22R in accordance with an operation or an instruction by the examiner or an instruction by the control unit 30.

In step S2, following the alignment adjustment in step S1, the control unit 30 simultaneously measures the corneal shapes of the left and right eyes to be examined EL and ER. Step S2 corresponds to a second measurement step of simultaneously performing the measurement using the second left eye measurement optical system and the measurement using the second right eye measurement optical system. In addition, "simultaneously measures the corneal shapes of the left and right eyes to be examined EL and ER" means that the control unit 30 simultaneously controls the keratometry system 34 of the left eye measurement optical system 25L and the keratometry system 34 of the right eye measurement optical system 25R to simultaneously acquire the measurement data of the corneal shape of the left eye to be examined EL and the measurement data of the corneal shape of the right eye to be examined ER. The control unit 30 stores the calculated measurement data of the corneal shapes of the left and right eyes to be examined EL and ER in the storage unit 30d.

Note that "simultaneous" includes not only a case in which timings are completely the same (that is, in a case in which there is no time difference), but also a case in which an allowable time difference is present. The allowable time difference may be, for example, either or both of a time difference according to the characteristics of the eyes to be examined and a time difference according to the characteristics of the ophthalmologic apparatus 10. The former can be determined, for example, clinically, and examples thereof include a time difference that is not affected by the eyeball movements of the eyes to be examined. The latter can be determined, for example, by actual measurement, and examples thereof include a time difference between controls of the ophthalmologic apparatus 10 and a time difference between operations of the ophthalmologic apparatus 10. Specific examples of "simultaneity" are as follows.

Suppose that two position measurements are performed instantaneously. In this case, when a time difference between a time of performing one position measurement and a time of performing the other position measurement is equal to or less than a predetermined threshold, it can be said that the two position measurements are "simultaneous".

In addition, suppose that one position measurement is performed instantaneously and the other position measurement is performed non-instantaneously. In this case, when the former position measurement is performed at any timing within a period in which the latter position measurement is performed, it can be said that the two position measurements are "simultaneous". In addition, even when a time difference between a timing at which the former position measurement is performed and a start timing or an end timing of the latter position measurement is equal to or less than a predetermined threshold, it can be said that the two position measurements are "simultaneous".

Furthermore, suppose that the two position measurements are performed non-instantaneously. In this case, when at least a part of a period in which one position measurement is performed and at least a part of a period in which the other position measurement is performed overlap, it can be said that the two position measurements are "simultaneous". In addition, even when a time difference between an end timing of one position measurement and a start timing of the other position measurement is equal to or less than a predetermined threshold, it can be said that the two position measurements are "simultaneous".

Note that the simultaneity described above may be expressed as "approximately simultaneous", "almost simultaneous", "substantially simultaneous", "substantial simultaneous", and the like.

In step S2, the control unit 30 calculates a corneal curvature radius by performing computation processing on the image acquired by the imaging element 31*g*, and calculates a corneal refractive power, a corneal astigmatism degree, and a corneal astigmatism axis angle from the calculated corneal curvature radius, to obtain the corneal shape.

In addition, in step S2, during the measurement of the corneal shapes, the control unit 30 causes the fixation projection systems 37 to present the fixation targets, to fix the lines of sight of the left and right eyes to be examined EL and ER. At this time, the fixation targets are presented at presentation positions at infinity to bring the left and right eyes to be examined EL and ER into a state of looking at infinity.

Moreover, in step S2, during the measurement of the corneal shapes, the control unit 30 measures distances from the eyes to be examined EL and ER to the respective objective lenses 26L and 26R. The control unit 30 stores the measurement data of the distances during the measurement of the corneal shapes, in the storage unit 30*d* as well. Here, the distance from the left eye to be examined EL to the objective lens 26L is measured on the basis of the images photographed by the two cameras 39A and 39B incorporated in the left housing 22*a*. Therefore, the two cameras 39A and 39B in the left housing 22*a* correspond to a left eye distance measurement unit that measures the distance from the left eye to be examined EL to the objective lens 26L (predetermined first reference position). In addition, the distance from the right eye to be examined ER to the objective lens 26R is measured on the basis of the images photographed by the two cameras 39A and 39B incorporated in the right housing

22*b*. Therefore, the two cameras 39A and 39B in the right housing 22*b* correspond to a right eye distance measurement unit that measures the distance from the right eye to be examined ER to the objective lens 26R (predetermined second reference position).

Hereinafter, a method of measuring the distances from the eyes to be examined EL and ER to the respective objective lenses 26L and 26R will be described. Since the same method of measuring the distance is adopted for the left and right eyes to be examined EL and ER, the method of measuring the distance from the left eye to be examined EL to the objective lens 26L will be described below.

First, under the control of the control unit 30, the two cameras 39A and 39B in the left housing 22*a* substantially simultaneously photograph the anterior eye segment images of the left eye to be examined EL from different directions. Subsequently, the control unit 30 corrects distortion or the like of the photographed images and analyzes the images in which the distortion has been corrected, thereby specifying a characteristic position of the left eye to be examined EL, for example, a position corresponding to a pupil center of the anterior eye segment. The control unit 30 then acquires three-dimensional position information of the left eye to be examined EL on the basis of the specified characteristic position (pupil center) of the left eye to be examined EL.

Figure 8:
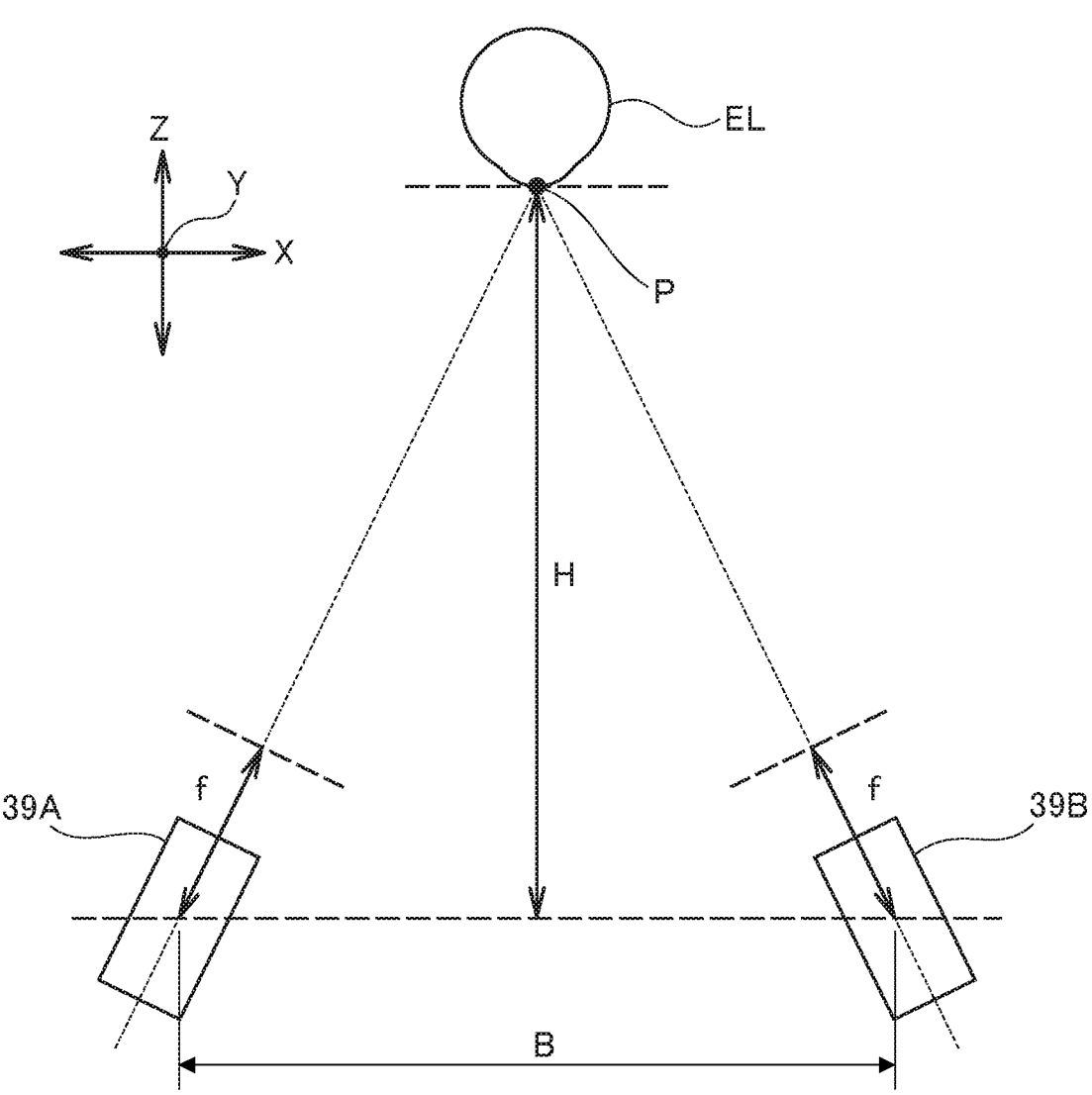
FIG. 8 is an explanatory diagram of a method of detecting an eye position, performed in the ophthalmologic apparatus of the first embodiment.

That is, as illustrated in FIG. 8, a distance (base line length) between the two cameras 39A and 39B is defined as "B". A distance (photographing distance) between a base line of the two cameras 39A and 39B and a characteristic part P of the left eye to be examined EL is defined as "H". A distance (screen distance) between each of the cameras 39A and 39B and a screen plane thereof is defined as "f".

In such a disposition state, resolution of the images photographed by the two cameras 39A and 39B is expressed by the following equations. Here, $\Delta p$ is pixel resolution.

Resolution in the $xy$ directions (plane resolution):
$$\Delta xy = H \times \Delta p / f$$

Resolution in the $z$ direction (depth resolution):
$$\Delta z = H \times H \times \Delta p / (B \times f)$$

The control unit 30 then calculates a three-dimensional position of the characteristic part P, that is, the distance from the left eye to be examined EL to the objective lens 26L by applying known trigonometry in consideration of a disposition relationship illustrated in FIG. 8 to the known positions of the two cameras 39A and 39B and the characteristic position corresponding to the characteristic part P in the two photographed images.

Furthermore, in step S2, the control unit 30 detects eye positions of the left eye to be examined EL and the right eye to be examined ER during the measurement of the corneal shapes. The control unit 30 stores the detection data of the eye positions during the measurement of the corneal shapes, in the storage unit 30*d* as well.

Here, the "eye positions" are rotation angles of the left and right eyes to be examined EL and ER about the eyeball revolution axes OL and OR. A rotation angle $\theta$ (eye position) is calculated on the basis of a change amount$=(R-r)\sin\theta$ of the position of the pupil center when the eyeball rotates by the rotation angle $\theta$, a change amount$=(R-d)\sin\theta$ of the position of the bright spot image (Br) in the anterior eye segment photographed image when the eyeball rotates by the rotation angle $\theta$, and a distance$=(r-d)\sin\theta$ between the pupil center and the bright spot image (Br) when the eyeball rotates by the rotation angle $\theta$. Note that "R" is a distance from the corneal apex to the rotation center of the eyeball, "r" is a curvature radius of the cornea, and "d" is a distance from the corneal apex to the pupil. When the rotation angle θ and a distance between the pupils of the examinee are obtained, a distance to an object visually recognized by convergence can be obtained.

In addition, it is not possible to accurately obtain biological data such as corneal distortion of the examinee, a pupil position, and a refractive index of components of the eye to be examined. Therefore, measurement for correcting the line-of-sight direction of the eye to be examined for estimating each parameter of the above equations may be performed before the measurement of the eye position. In the measurement for correction, a visual target is presented at a position that can be clearly viewed by the eye to be examined, an anterior eye segment image when the presented visual target is viewed is acquired, and the pupil center and the bright spot image (Br) are acquired. The rotation angle from the pupil center and the bright spot image (Br) at this time is corrected using the rotation angle of the presented visual target.

In step S3, following the measurement of the corneal shapes in step S2, the control unit 30 simultaneously measures the refractive properties of the left and right eyes to be examined EL and ER. Step S3 corresponds to a third measurement step of simultaneously performing the measurement using the third left eye measurement optical system and the measurement using the third right eye measurement optical system. In addition, "simultaneously measures the refractive properties of the left and right eyes to be examined EL and ER" means that the control unit 30 simultaneously controls the reflex measurement projection system 35 and the reflex measurement light receiving system 36 of the left eye measurement optical system 25L and the reflex measurement projection system 35 and the reflex measurement light receiving system 36 of the right eye measurement optical system 25R to simultaneously acquire the measurement data of the refractive property of the left eye to be examined EL and the measurement data of the refractive property of the right eye to be examined ER. Note that "simultaneous" is as described above. The control unit 30 stores, in the storage unit 30d, the measurement data of the refractive properties of the left and right eyes to be examined EL and ER obtained by the measurement.

In step S3, the control unit 30 analyzes the ring image (pattern image) obtained by the imaging element 31g receiving the reflected light (fundus return light) of the ring-shaped measurement light flux projected onto the eye fundus Ef by the reflex measurement projection system 35. By this analysis, a spherical degree, an astigmatism degree, and an astigmatism axis angle (refractive property) are obtained. The control unit 30 stores the calculated measurement data of the refractive property in the storage unit 30d. In the analysis of the ring image by the control unit 30, for example, first, a barycentric position of the ring image is obtained from a luminance distribution in an image in which the obtained ring image is shown, luminance distributions along a plurality of scanning directions radially extending from the barycentric position are obtained, and the ring image is specified from the luminance distributions. Subsequently, an approximate ellipse of the specified ring image is obtained, and a major axis and a minor axis of the approximate ellipse are substituted into a known equation to obtain the spherical degree, the astigmatism degree, and the astigmatism axis angle. In addition, the control unit 30 may obtain the refractive property on the basis of deformation and displacement of the ring image with respect to a reference pattern.

In addition, in step S3, during the measurement of the refractive properties, the control unit 30 causes the fixation projection systems 37 to present the fixation targets, to fix the lines of sight of the left and right eyes to be examined EL and ER. At this time, the fixation targets are presented at presentation positions at infinity to bring the left and right eyes to be examined EL and ER into a state of looking at infinity. In addition, the control unit 30 may move the relay lenses 37b to far points of the left and right eyes to be examined EL and ER on the basis of a result of tentative measurement of the refractive properties, and then move the relay lenses 37b to positions out of focus to bring the eyes into a foggy state. As a result, the left and right eyes to be examined EL and ER enter an accommodation resting state (crystalline lens accommodation relieved state), and the refractive properties can be measured in the accommodation resting state.

Moreover, in step S3, during the measurement of the refractive properties, the control unit 30 measures distances from the eyes to be examined EL and ER to the respective objective lenses 26L and 26R. The control unit 30 stores the measurement data of the distances during the measurement of the refractive properties, in the storage unit 30d as well. Note that the "method of measuring the distance" is as described above.

Furthermore, in step S3, the control unit 30 detects eye positions of the left eye to be examined EL and the right eye to be examined ER during the measurement of the refractive properties. The control unit 30 stores the detection data of the eye positions during the measurement of the refractive properties, in the storage unit 30d as well. Note that the "eye positions" are as described above.

In step S4, following the measurement of the refractive properties in step S3, the control unit 30 simultaneously measures the eye axial lengths of the left and right eyes to be examined EL and ER. Step S4 corresponds to a first measurement step of simultaneously performing the measurement using the first left eye measurement optical system and the measurement using the first right eye measurement optical system. In addition, "simultaneously measures the eye axial lengths of the left and right eyes to be examined EL and ER" means that the control unit 30 almost simultaneously performs photographing of the anterior eye segments of the left and right eyes to be examined EL and ER and OCT scanning of the eye fundi Ef of the left and right eyes to be examined EL and ER to simultaneously acquire the measurement data of the eye axial length of the left eye to be examined EL and the measurement data of the eye axial length of the right eye to be examined ER. Note that "simultaneous" is as described above. The control unit 30 stores, in the storage unit 30d, the measurement data of the eye axial lengths of the left and right eyes to be examined EL and ER obtained by the measurement.

In the photographing of the anterior eye segments in step S4, for example, the anterior eye segments of the left and right eyes to be examined EL and ER on which the alignment light fluxes are projected by the XY alignment systems 33 are each photographed by the two cameras 39A and 39B. In addition, in the OCT scanning, for example, A-scanning (or B-scanning, three-dimensional scanning, or another scan mode) is performed by the OCT optical systems 38. The control unit 30 constructs OCT data from the data collected by the fundus OCT scanning. The OCT data is, for example, a reflection intensity profile or image data.

Next, the control unit 30 acquires data indicating the arm length (for example, the position of the corner cube 114) when the OCT scanning is performed. Subsequently, the control unit 30 analyzes the anterior eye segment photo-graphed image, specifies the position of the bright spot image (Br) in the anterior eye segment photographed image, and sets a reference position (first reference position) in the anterior eye segment photographed image on the basis of the corneal curvature radius acquired in step S2. Subsequently, the control unit 30 calculates position displacement (first displacement) of the bright spot image with respect to the first reference position, and calculates an alignment error between each of the left and right eyes to be examined EL and ER and the measurement arm corresponding to the first displacement. Subsequently, a change amount of the arm length with respect to a reference arm length stored in advance is calculated. Subsequently, the control unit 30 specifies a coherence gate position corresponding to the arm length, and sets the specified coherence gate position as a reference position (second reference position) in the OCT data. Subsequently, the control unit 30 analyzes the OCT data to specify a data position (retinal surface position) corresponding to a retinal surface of each of the left and right eyes to be examined EL and ER. Subsequently, the control unit 30 calculates displacement (second displacement) of the retinal surface position with respect to the second reference position. The control unit 30 then performs computation on the basis of a reference eye axial length stored in advance, the alignment error, the arm length change amount, and the second displacement, thereby obtaining a measurement value of the eye axial length of the eye to be examined E.

In addition, in step S4, during the measurement of the eye axial lengths, the control unit 30 causes the fixation projec-tion systems 37 to present the fixation targets, to fix the lines of sight of the left and right eyes to be examined EL and ER. At this time, the fixation targets are presented at presentation positions at infinity to bring the left and right eyes to be examined EL and ER into a state of looking at infinity.

Furthermore, in step S4, the control unit 30 detects eye positions of the left eye to be examined EL and the right eye to be examined ER during the measurement of the eye axial lengths. The control unit 30 stores the detection data of the eye positions during the measurement of the eye axial lengths, in the storage unit 30*d* as well. Note that the "eye positions" are as described above.

In step S5, following the measurement of the eye axial lengths in step S4, the control unit 30 reads the reference data stored in advance in the storage unit 30*d*. Step S5 corresponds to a reading step of reading the reference data from the storage unit 30*d* storing the reference data after obtaining the measurement data.

In step S6, following the reading of the reference data in step S5, the control unit 30 reads the measurement data stored in the storage unit 30*d* and compares the reference data and the measurement data. Step S6 corresponds to a comparison step of comparing the reference data and the measurement data.

In step S7, following the comparison of the data in step S6, the comparison result is output. Note that the compari-son result is displayed on the display device 19*c* of the examiner controller 19*a*. Step S7 corresponds to an output step of outputting the comparison result.

Hereinafter, features and operations of the ophthalmo-logic apparatus 10 of the first embodiment will be described.

The ophthalmologic apparatus 10 of the first embodiment includes the OCT optical system 38 of the left eye measure-ment optical system 25L used for measuring the eye axial length of the left eye to be examined EL, the keratometry system 34 of the left eye measurement optical system 25L used for measuring the corneal shape of the left eye to be examined EL, and the reflex measurement optical system (the reflex measurement projection system 35 and the reflex measurement light receiving system 36) of the left eye measurement optical system 25L used for measuring the refractive property of the left eye to be examined EL. In addition, the ophthalmologic apparatus 10 of the first embodiment includes the OCT optical system 38 of the right eye measurement optical system 25R used for measuring the eye axial length of the right eye to be examined ER, the keratometry system 34 of the right eye measurement optical system 25R used for measuring the corneal shape of the right eye to be examined ER, and the reflex measurement optical system (the reflex measurement projection system 35 and the reflex measurement light receiving system 36) of the right eye measurement optical system 25R used for mea-suring the refractive property of the right eye to be examined ER.

In the case of measuring the eye characteristics of the eyes to be examined in the ophthalmologic apparatus 10 of the first embodiment, first, the control unit 30 controls the Z alignment systems 32, the XY alignment systems 33, and the anterior eye segment observation systems 31, to dispose the left eye measurement head 22L and the right eye measure-ment head 22R at the examination positions (step S1 of the flowchart illustrated in FIG. 7).

Subsequently, the process sequentially proceeds to step S2, step S3, and step S4 of the flowchart illustrated in FIG. 7. That is, the control unit 30 controls each of the OCT optical system 38, the keratometry system 34, and the reflex measurement optical system (the reflex measurement pro-jection system 35 and the reflex measurement light receiving system 36) of the left eye measurement optical system 25L, and the two cameras 39A and 39B provided in the left housing 22*a*, and each of the OCT optical system 38, the keratometry system 34, and the reflex measurement optical system (the reflex measurement projection system 35 and the reflex measurement light receiving system 36) of the right eye measurement optical system 25R, and the two cameras 39A and 39B provided in the right housing 22*b*. The measurement of the corneal shapes is simultaneously per-formed in the left and right eyes to be examined EL and ER, the measurement of the refractive properties is simultane-ously performed in the left and right eyes to be examined EL and ER, and the measurement of the eye axial lengths is simultaneously performed in the left and right eyes to be examined EL and ER.

As a result, the ophthalmologic apparatus 10 of the first embodiment can measure the eye characteristics (eye axial lengths, corneal shapes, refractive properties) of the left and right eyes to be examined EL and ER under almost the same conditions in a state in which both the eyes are open. This makes it possible to measure the eye characteristics of the left and right eyes to be examined EL and ER in a state close to a daily life state in which an object is visually recognized using both the left and right eyes, to appropriately measure the eye characteristics.

In addition, in the ophthalmologic apparatus 10 of the first embodiment, the OCT optical system 38, the keratometry system 34, and the reflex measurement optical system (the reflex measurement projection system 35 and the reflex measurement light receiving system 36) of the left eye measurement optical system 25L are housed in the left housing 22*a* of the left eye measurement head 22L. In addition, the OCT optical system 38, the keratometry system 34, and the reflex measurement optical system (the reflex measurement projection system 35 and the reflex measure-ment light receiving system 36) of the right eye measurement optical system 25R are housed in the right housing 22*b* of the right eye measurement head 22R. The control unit 30 individually drives the left drive mechanism 21L and the right drive mechanism 21R, to control the positions in the XYZ directions of the left eye measurement head 22L (left housing 22*a*) and the right eye measurement head 22R (right housing 22*b*), and the directions thereof having the eyeball revolution axes OL and OR as the center positions.

As a result, the optical systems 38, 34, 35, and 36 can move integrally with respect to the corresponding left and right eyes to be examined EL and ER, and can easily perform adjustment such as alignment. In addition, since it is only necessary to provide one drive mechanism (the left drive mechanism 21L, the right drive mechanism 21R) for driving each of the left and right measurement heads 22L and 22R housing the optical systems 38, 34, 35, and 36 on each of the left and right sides, the device can be made compact.

In addition, in the ophthalmologic apparatus 10 of the first embodiment, the control unit 30 includes the storage unit 30*d* that stores the reference data in advance. After the pieces of measurement data of the corneal shapes, the refractive properties, and the eye axial lengths of the left and right eyes to be examined EL and ER are acquired, the process sequentially proceeds to step S5, step S6, and step S7 of the flowchart illustrated in FIG. 7. That is, the control unit 30 reads the reference data stored in the storage unit 30*d*, compares the read reference data and the measurement data of the eye characteristics (eye axial lengths, corneal shapes, refractive properties) of the left and right eyes to be examined EL and ER obtained by simultaneously measuring the left and right eyes to be examined EL and ER, and outputs the comparison results. As a result, by recognizing the comparison results displayed on the display device 19*c* or the like, the examiner can easily evaluate how much the left and right eyes to be examined EL and ER measured by the ophthalmologic apparatus 10 deviate from the reference data on the basis of the comparison results, whether a known symptom is already exhibited, and the like.

In addition, in the ophthalmologic apparatus 10 of the first embodiment, the OCT optical system 38, the keratometry system 34, and the reflex measurement optical system (the reflex measurement projection system 35 and the reflex measurement light receiving system 36) of the left eye measurement optical system 25L have the common left eye measurement axis LL. In addition, since the configuration of the left eye measurement optical system 25L and the configuration of the right eye measurement optical system 25R are identical, the OCT optical system 38, the keratometry system 34, and the reflex measurement optical system (the reflex measurement projection system 35 and the reflex measurement light receiving system 36) of the right eye measurement optical system 25R have the common right eye measurement axis LR.

As a result, by aligning the common left eye measurement axis LL and the common right eye measurement axis LR with respect to the left and right eyes to be examined EL and ER, the alignment of the OCT optical systems 38, the keratometry systems 34, and the reflex measurement optical systems (the reflex measurement projection systems 35 and the reflex measurement light receiving systems 36) can be completed. In addition, since the optical systems 38, 34, 35, and 36 are aligned at the same time, the measurements using the optical systems 38, 34, 35, and 36 can be performed under the same alignment conditions, and the measurement data can be obtained in a comparable form with high accuracy. Moreover, it is possible to share the optical components, and to reduce the number of components.

In addition, in the ophthalmologic apparatus 10 of the first embodiment, the two cameras 39A and 39B that measure the distance from the left eye to be examined EL to the objective lens 26L are provided in the left housing 22*a*, and the two cameras 39A and 39B that measure the distance from the right eye to be examined ER to the objective lens 26R are provided in the right housing 22*b*. In step S2, the control unit 30 measures the distance from the left eye to be examined EL to the objective lens 26L and the distance from the right eye to be examined ER to the objective lens 26R during the measurement of the corneal shapes using the keratometry systems 34. In addition, in step S3, the control unit 30 measures the distance from the left eye to be examined EL to the objective lens 26L and the distance from the right eye to be examined ER to the objective lens 26R during the measurement of the refractive properties using the reflex measurement optical systems (the reflex measurement projection systems 35 and the reflex measurement light receiving systems 36).

As a result, it is possible to determine whether or not the distances from the left and right eyes to be examined EL and ER to the objective lenses 26L and 26R are distances suitable for the measurement of the corneal shapes and the refractive properties, and it is possible to measure the corneal shapes and the refractive properties on the basis of results of the determination. Therefore, more accurate measurement can be performed. In addition, it is possible to output highly accurate comparison results when performing comparison with the reference data.

In addition, the ophthalmologic apparatus 10 of the first embodiment includes the fixation projection system 37 of the left eye measurement optical system 25L used for fixation of the left eye to be examined EL, and the fixation projection system 37 of the right eye measurement optical system 25R used for fixation of the right eye to be examined ER. In step S2, the control unit 30 causes the keratometry systems 34 to measure the corneal shapes in a state in which the left eye to be examined EL is fixed using the fixation projection system 37 of the left eye measurement optical system 25L and the right eye to be examined ER is fixed using the fixation projection system 37 of the right eye measurement optical system 25R. In addition, in step S3, the control unit 30 causes the reflex measurement optical systems (the reflex measurement projection systems 35 and the reflex measurement light receiving systems 36) to measure the refractive properties in a state in which the left eye to be examined EL is fixed using the fixation projection system 37 of the left eye measurement optical system 25L and the right eye to be examined ER is fixed using the fixation projection system 37 of the right eye measurement optical system 25R. Furthermore, in step S4, the control unit 30 causes the OCT optical systems 38 and the two cameras 39A and 39B to measure the eye axial lengths in a state in which the left eye to be examined EL is fixed using the fixation projection system 37 of the left eye measurement optical system 25L and the right eye to be examined ER is fixed using the fixation projection system 37 of the right eye measurement optical system 25R.

As a result, the left and right eyes to be examined EL and ER can be focused on the fixation targets, and the lines of sight of the left and right eyes to be examined EL and ER can be fixed. Here, it is essential for accurate measurement to set the line-of-sight directions (visual axes) of the left and right eyes to be examined EL and ER to correct positions with respect to the left eye measurement axis LL and the right eye measurement axis LR. That is, by fixing the lines of sight of the left and right eyes to be examined EL and ER in a desired direction (infinity in the first embodiment), the visual axes can be aligned with the left eye measurement axis LL and the right eye measurement axis LR, and measurement accuracy of the eye characteristics can be improved.

In addition, in the ophthalmologic apparatus 10 of the first embodiment, the OCT optical systems 38 used for measuring the eye axial lengths (dimensional information in the front-back direction) of the left and right eyes to be examined EL and ER constitute the interferometry measurement mechanisms. Therefore, it is not necessary to bring a probe into contact with the eyeball as in a case in which eye axis measurement is performed using ultrasonic waves, for example, and it is possible to prevent occurrence of a measurement error due to eyeball compression. In addition, ocular anesthesia can also be dispensed with. As a result, the eye axial lengths of the left and right eyes to be examined EL and ER can be measured with high accuracy.

In particular, the OCT optical system 38 of the first embodiment is an interferometer using optical coherence interferometry. Therefore, the measurement of the eye axial lengths can be performed using light having a relatively short coherence length, and the OCT optical systems 38 can be prevented from having an unnecessarily long optical path length.

In addition, in the ophthalmologic apparatus 10 of the first embodiment, the keratometry systems 34 used for measuring the corneal shapes of the left and right eyes to be examined EL and ER constitute the keratometer mechanisms. Therefore, the control unit 30 can cause measurement of the corneal shapes on the basis of the images obtained by photographing the reflected light of the ring-shaped light fluxes (light fluxes for corneal shape measurement) projected onto the left and right eyes to be examined EL and ER.

In particular, the keratometry systems 34 of the first embodiment include the kerato plates 34a and the kerato ring light sources 34b that project the ring-shaped light fluxes for corneal shape measurement onto the corneas Cr of the left and right eyes to be examined EL and ER. The control unit 30 analyzes the images obtained by photographing the anterior eye segments of the left and right eyes to be examined EL and ER in which the pattern images of the ring-shaped light fluxes are formed, to obtain the corneal shapes. As a result, the corneal shapes can be easily obtained by so-called image processing.

In addition, in the ophthalmologic apparatus 10 of the first embodiment, the reflex measurement optical systems (the reflex measurement projection systems 35 and the reflex measurement light receiving systems 36) used for the measurement of the refractive properties of the left and right eyes to be examined EL and ER constitute the auto refractometer mechanisms. Therefore, the refractive properties of the left and right eyes to be examined EL and ER can be easily measured.

In particular, the reflex measurement optical systems of the first embodiment include the reflex measurement projection systems 35 that project the measurement light fluxes (light fluxes for refractive property measurement) onto the eye fundi Ef of the left and right eyes to be examined EL and ER, and the reflex measurement light receiving systems 36 that receive the measurement light fluxes reflected from the eye fundi Ef of the left and right eyes to be examined EL and ER. As a result, the refractive properties such as the refractive power values can be calculated by projecting the light fluxes for refractive property measurement onto the eye fundi Ef, receiving the reflected images from the eye fundi Ef, and performing computation processing by the control unit 30.

In the ophthalmologic apparatus 10 of the first embodiment, the control unit 30 detects the eye positions of the left and right eyes to be examined EL and ER at the time of measuring the corneal shapes using the keratometry systems 34 in step S2. In addition, the control unit 30 detects the eye positions of the left and right eyes to be examined EL and ER at the time of measuring the refractive properties using the reflex measurement optical systems (the reflex measurement projection systems 35 and the reflex measurement light receiving systems 36) in step S3. Furthermore, the control unit 30 detects the eye positions of the left and right eyes to be examined EL and ER at the time of measuring the eye axial lengths using the OCT optical systems 38 and the two cameras 39A and 39B in step S4.

As a result, it is possible to grasp the eye positions during the measurement of the respective eye characteristics, and it is possible to recognize the validity, accuracy, and the like of the measurement data obtained by the measurement. In addition, depending on the state of the eye positions, it is possible to perform the measurement again, and the like, and the measurement accuracy can be improved.

Although the ophthalmologic apparatus of the present invention has been described on the basis of the first embodiment, the specific configuration is not limited to this embodiment, and design modifications, additions, and the like are allowed without departing from the gist of the invention according to each claim of the claims.

For example, in the first embodiment, an example has been described in which the corneal position is measured using the two cameras 39A and 39B and the retinal position is measured using the OCT optical system 38 at the time of measuring the eye axial length as the dimensional information in the front-back direction of each of the left and right eyes to be examined EL and ER, but the present invention is not limited thereto. For example, as described in JP 2017-189669 A and the like, both the corneal position and the retinal position may be measured using the OCT optical system 38.

In addition, for the ophthalmologic apparatus 10 of the first embodiment, an example has been described in which the distances from the left and right eyes to be examined EL and ER to the objective lenses 26L and 26R are measured in both the measurement of the corneal shapes and the measurement of the refractive properties, but the present invention is not limited thereto. The distances from the eyes to be examined EL and ER to the respective objective lenses 26L and 26R may be detected during at least one of the measurement of the corneal shapes and the measurement of the refractive properties. Note that the distances from the eyes to be examined EL and ER to the respective objective lenses 26L and 26R do not necessarily have to be detected.

In addition, in the first embodiment, the first reference position at the time of detecting the distance is set to the objective lens 26R provided in the left eye measurement head 22L, and the second reference position is set to the objective lens 26L provided in the right eye measurement head 22R, but the present invention is not limited thereto. The reference positions can be set to any position, for example, a center position of the two cameras 39A and 39B, or the like. In addition, the left eye distance measurement unit and the right eye distance measurement unit may be constituted by, for example, any distance sensor or the like.

In addition, for the ophthalmologic apparatus 10 of the first embodiment, an example has been described in which the left and right eyes to be examined EL and ER are fixed in all of the measurement of the eye axial lengths, the measurement of the corneal shapes, and the measurement of the refractive properties. However, the present invention is not limited thereto, and the left and right eyes to be examined EL and ER may be fixed in at least one of the measurement of the eye axial lengths, the measurement of the corneal shapes, and the measurement of the refractive properties. In addition, it is not always necessary to perform the fixation using the fixation projection systems 37.

For the ophthalmologic apparatus 10 of the first embodiment, an example has been described in which the corneal shapes of the left and right eyes to be examined EL and ER are simultaneously measured on the left and right sides, the refractive properties of the left and right eyes to be examined EL and ER are then simultaneously measured on the left and right sides, and the eye axial lengths of the left and right eyes to be examined EL and ER are finally simultaneously measured on the left and right sides. That is, each eye characteristic is simultaneously measured on the left and right sides, and these eye characteristics are sequentially measured. However, the present invention is not limited thereto. For example, the corneal shapes of the left and right eyes to be examined EL and ER may be simultaneously measured on the left and right sides, and at the same time, the refractive properties of the left and right eyes to be examined EL and ER may be simultaneously measured on the left and right sides. Furthermore, the eye axial lengths may be measured at the same time as the corneal shapes or the refractive properties, or all the eye characteristics may be measured at the same time.

Furthermore, the measurement order of the eye axial lengths, the corneal shapes, and the refractive properties is not limited to the order described in the first embodiment, and can be optionally determined. In addition, the alignment may be finely adjusted between the measurements of the eye axial lengths, the corneal shapes, and the refractive properties.

The invention claimed is:

1. An ophthalmologic apparatus comprising:
a first left eye measurement optical system used for measurement of dimensional information in a front-back direction of a left eye to be examined;
a second left eye measurement optical system used for measurement of a corneal shape of the left eye to be examined;
a third left eye measurement optical system used for measurement of a refractive property of the left eye to be examined;
a first right eye measurement optical system used for measurement of dimensional information in a front-back direction of a right eye to be examined;
a second right eye measurement optical system used for measurement of a corneal shape of the right eye to be examined;
a third right eye measurement optical system used for measurement of a refractive property of the right eye to be examined; and
a control unit configured to control the first left eye measurement optical system, the second left eye measurement optical system, the third left eye measurement optical system, the first right eye measurement optical system, the second right eye measurement optical system, and the third right eye measurement optical system, and process measurement data obtained using each of the optical systems, wherein the control unit simultaneously causes the measurement using the first left eye measurement optical system and the measurement using the first right eye measurement optical system,
simultaneously causes the measurement using the second left eye measurement optical system and the measurement using the second right eye measurement optical system,
simultaneously causes the measurement using the third left eye measurement optical system and the measurement using the third right eye measurement optical system,
determines validity of the measurement data obtained by using the third left eye measurement optical system with the measurement data obtained by using the first left eye measurement optical system and/or the measurement data obtained by using the second left eye measurement optical system, and
determines validity of the measurement data obtained by using the third right eye measurement optical system with the measurement data obtained by using the first right eye measurement optical system and/or the measurement data obtained by using the second right eye measurement optical system.

2. The ophthalmologic apparatus according to claim 1, wherein
the first left eye measurement optical system, the second left eye measurement optical system, and the third left eye measurement optical system are housed in a left-eye housing,
the first right eye measurement optical system, the second right eye measurement optical system, and the third right eye measurement optical system are housed in a right-eye housing, and
the control unit controls a position and a direction of each of the left-eye housing and the right-eye housing.

3. The ophthalmologic apparatus according to claim 1, further comprising
a storage unit configured to store reference data, wherein
the control unit compares the reference data read from the storage unit and the measurement data, and outputs a comparison result.

4. The ophthalmologic apparatus according to claim 1, wherein
the first left eye measurement optical system, the second left eye measurement optical system, and the third left eye measurement optical system have a common left eye measurement axis, and
the first right eye measurement optical system, the second right eye measurement optical system, and the third right eye measurement optical system have a common right eye measurement axis.

5. The ophthalmologic apparatus according to claim 1, further comprising:
a left eye distance measurement unit configured to measure a distance from the left eye to be examined to a predetermined first reference position; and
a right eye distance measurement unit configured to measure a distance from the right eye to be examined to a predetermined second reference position, wherein
the control unit causes the left eye distance measurement unit to measure the distance from the left eye to be examined to the first reference position during the measurement using at least one of the second left eye measurement optical system or the third left eye measurement optical system, and causes the right eye distance measurement unit to measure the distance from the right eye to be examined to the second reference position during the measurement using at least one of the second right eye measurement optical system or the third right eye measurement optical system.

6. The ophthalmologic apparatus according to claim 1, further comprising:

a left eye fixation optical system used for fixation of the left eye to be examined; and a right eye fixation optical system used for fixation of the right eye to be examined, wherein the control unit causes the measurement using at least one of the first left eye measurement optical system, the second left eye measurement optical system, or the third left eye measurement optical system in a state in which the left eye to be examined is fixed using the left eye fixation optical system, and causes the measurement using at least one of the first right eye measurement optical system, the second right eye measurement optical system, or the third right eye measurement optical system in a state in which the right eye to be examined is fixed using the right eye fixation optical system.

7. The ophthalmologic apparatus according to claim 1, wherein the first left eye measurement optical system and the first right eye measurement optical system constitute an interferometry measurement mechanism.

8. The ophthalmologic apparatus according to claim 7, wherein the interferometry measurement mechanism is an interferometer using optical coherence interferometry.

9. The ophthalmologic apparatus according to claim 1, wherein the second left eye measurement optical system and the second right eye measurement optical system constitute a keratometer mechanism.

10. The ophthalmologic apparatus according to claim 9, wherein the keratometer mechanism includes a kerato projection system configured to project a light flux for corneal shape measurement onto a cornea of the left eye to be examined or the right eye to be examined, and the control unit obtains the corneal shape on a basis of an image obtained by photographing an anterior eye segment of the left eye to be examined or the right eye to be examined in which a pattern image is formed by the projected light flux for corneal shape measurement.

11. The ophthalmologic apparatus according to claim 1, wherein the third left eye measurement optical system and the third right eye measurement optical system constitute an auto refractometer mechanism.

12. The ophthalmologic apparatus according to claim 11, wherein the auto refractometer mechanism includes a reflex measurement projection system configured to project a light flux for refractive property measurement onto an eye fundus of the left eye to be examined or the right eye to be examined, and a reflex measurement light receiving system configured to receive the light flux for refractive property measurement reflected from the eye fundus of the left eye to be examined or the right eye to be examined.

13. The ophthalmologic apparatus according to claim 1, wherein the control unit detects eye positions of the left eye to be examined and the right eye to be examined during the measurement using the first left eye measurement optical system and the first right eye measurement optical system, during the measurement using the second left eye measurement optical system and the second right eye measurement optical system, and during the measurement using the third left eye measurement optical system and the third right eye measurement optical system.

14. A method of examining an eye to be examined by an ophthalmologic apparatus including:

a first left eye measurement optical system used for measurement of dimensional information in a front-back direction of a left eye to be examined;

a second left eye measurement optical system used for measurement of a corneal shape of the left eye to be examined;

a third left eye measurement optical system used for measurement of a refractive property of the left eye to be examined;

a first right eye measurement optical system used for measurement of dimensional information in a front-back direction of a right eye to be examined;

a second right eye measurement optical system used for measurement of a corneal shape of the right eye to be examined;

a third right eye measurement optical system used for measurement of a refractive property of the right eye to be examined; and a control unit configured to control the first left eye measurement optical system, the second left eye measurement optical system, the third left eye measurement optical system, the first right eye measurement optical system, the second right eye measurement optical system, and the third right eye measurement optical system, and process measurement data obtained using each of the optical systems, the method comprising:

a first measurement step of simultaneously performing the measurement using the first left eye measurement optical system and the measurement using the first right eye measurement optical system;

a second measurement step of simultaneously performing the measurement using the second left eye measurement optical system and the measurement using the second right eye measurement optical system;

a third measurement step of simultaneously performing the measurement using the third left eye measurement optical system and the measurement using the third right eye measurement optical system;

a step of determining validity of the measurement data obtained by using the third left eye measurement optical system with the measurement data obtained by using the first left eye measurement optical system and/or the measurement data obtained by using the second left eye measurement optical system; and a step of determining validity of the measurement data obtained by using the third right eye measurement optical system with the measurement data obtained by using the first right eye measurement optical system and/or the measurement data obtained by using the second right eye measurement optical system.

15. The method of examining an eye to be examined according to claim 14, the method further comprising:

a reading step of reading reference data from a storage unit that stores the reference data after obtaining the measurement data in the first measurement step, the second measurement step, and the third measurement step;

a comparison step of comparing the reference data read in the reading step and the measurement data; and an output step of outputting a comparison result obtained from the comparison step.

16. The method of examining an eye to be examined according to claim 14, wherein in the first measurement step, eye positions of the left eye to be examined and the right eye to be examined are detected during the measurement using the first left eye measurement optical system and the first right eye measurement optical system, in the second measurement step, eye positions of the left eye to be examined and the right eye to be examined are detected during the measurement using the second left eye measurement optical system and the second right eye measurement optical system, and in the third measurement step, eye positions of the left eye to be examined and the right eye to be examined are detected during the measurement using the third left eye measurement optical system and the third right eye measurement optical system.

* * * * *